(12) United States Patent
Oomuro et al.

(10) Patent No.: US 9,604,891 B2
(45) Date of Patent: Mar. 28, 2017

(54) METHODS FOR PRODUCING FLUORINE-CONTAINING HYDROXYALDEHYDE, FLUORINE-CONTAINING PROPANEDIOL, AND FLUORINE-CONTAINING ALCOHOL MONOMER

(71) Applicant: Central Glass Company, Limited, Ube-shi, Yamaguchi (JP)

(72) Inventors: Hitoshi Oomuro, Saitama (JP); Ryo Nadano, Saitama (JP); Masafumi Hirotsu, Fujimino (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 14/660,401

(22) Filed: Mar. 17, 2015

(65) Prior Publication Data

US 2015/0361026 A1    Dec. 17, 2015

(30) Foreign Application Priority Data

Mar. 18, 2014  (JP) ................. 2014-054543
Mar. 5, 2015   (JP) ................. 2015-043123

(51) Int. Cl.
| | |
|---|---|
| C07C 29/141 | (2006.01) |
| C07C 45/72  | (2006.01) |
| C07C 67/08  | (2006.01) |
| C08F 220/22 | (2006.01) |
| C08F 220/28 | (2006.01) |
| C08L 33/14  | (2006.01) |
| G03F 7/00   | (2006.01) |

(52) U.S. Cl.
CPC ............ *C07C 29/141* (2013.01); *C07C 45/72* (2013.01); *C07C 67/08* (2013.01); *C08F 220/22* (2013.01); *C08F 220/28* (2013.01); *C08L 33/14* (2013.01); *G03F 7/00* (2013.01)

(58) Field of Classification Search
CPC ....... C07C 29/141; C07C 45/72; C07C 67/08; C08F 220/22; C08F 220/28; C08L 33/14; G03F 7/00
See application file for complete search history.

(56) References Cited

U.S. PATENT DOCUMENTS

| | | | |
|---|---|---|---|
| 3,440,285 A | 4/1969 | Lichstein et al. | |
| 3,642,904 A * | 2/1972 | Langkammerer | C07C 45/66 514/890 |
| 4,704,479 A | 11/1987 | Warnes et al. | |
| 8,729,316 B2 | 5/2014 | Mazzell, Jr. et al. | |
| 2005/0215836 A1 | 9/2005 | Komata et al. | |
| 2009/0208873 A1 | 8/2009 | Harada et al. | |
| 2012/0021359 A1 | 1/2012 | Hayama et al. | |

FOREIGN PATENT DOCUMENTS

| | | |
|---|---|---|
| CN | 103429560 A | 12/2013 |
| JP | 2005-239710 A | 9/2005 |
| JP | 2009-51805 A | 3/2009 |
| JP | 2013-84950 A | 5/2013 |
| TW | 200936616 A | 9/2009 |
| WO | WO 2011/145663 A1 | 11/2011 |
| WO | WO 2012/112751 A1 | 8/2012 |

OTHER PUBLICATIONS

Taiwanese Office Action issued in Taiwanese Application No. 10520006540 dated Jan. 6, 2016 (six pages).
Trost et al., "The Direct Catalytic Asymmetric Aldol Reaction" NIH Public Access, May 2010, four pages, Chem Soc Rev., 39(5): 1600-1632.
Korean-language Office Action issued in counterpart Korean Application No. 10-2015-0037409 dated Dec. 6, 2016 (five (5) pages).

* cited by examiner

Primary Examiner — Paul A Zucker
Assistant Examiner — Mark Luderer
(74) Attorney, Agent, or Firm — Crowell & Moring LLP

(57) ABSTRACT

As shown by the following reaction formula, disclosed is a fluorine-containing hydroxyaldehyde production method, including the step of obtaining a fluorine-containing hydroxyaldehyde represented by the general formula (1) by reacting a fluorine-containing ketone represented by the general formula (4) and an aldehyde represented by the general formula (5) in the presence of an organic base selected from a heterocyclic compound which contains a nitrogen atom in its ring or a tertiary amine. By this production method, it is possible to obtain the fluorine-containing hydroxyaldehyde in a high yield. Furthermore, it is possible to easily obtain in high yields a fluorine-containing propanediol, which is a derivative of this fluorine-containing hydroxyaldehyde, and a fluorine-containing alcohol monomer by using the same.

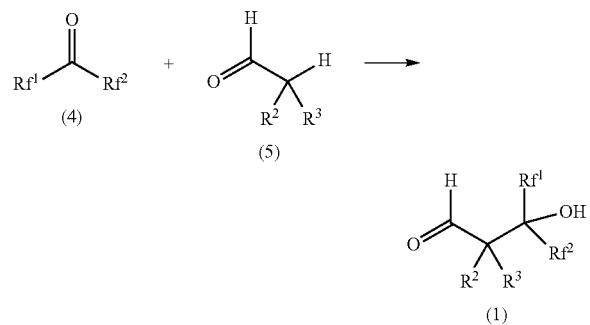

15 Claims, No Drawings

METHODS FOR PRODUCING FLUORINE-CONTAINING HYDROXYALDEHYDE, FLUORINE-CONTAINING PROPANEDIOL, AND FLUORINE-CONTAINING ALCOHOL MONOMER

TECHNICAL FIELD

The present invention relates to methods for producing a fluorine-containing hydroxyaldehyde, a fluorine-containing propanediol, and a fluorine-containing alcohol monomer. Specifically, it relates to a new method for producing a fluorine-containing hydroxyaldehyde by reacting a fluorine-containing ketone and an aldehyde compound under a particular condition. It relates to a method in which the fluorine-containing hydroxyaldehyde is reduced to obtain a desired fluorine-containing propanediol, and then from the fluorine-containing propanediol a fluorine-containing alcohol monomer is produced. The fluorine-containing monomer is useful as a raw material of resists.

BACKGROUND OF THE INVENTION

A fluorine-containing polymer made from a fluorine-containing alcohol monomer, in the field of producing semiconductors, can be used for, for example, topcoat of immersion lithography for its superior solubility in the developing solution (tetramethylammonium hydroxide, hereinafter it may be abbreviated as TMAH). A topcoat is a protective film to protect a resist film from chemical substances such as amines in the environment where lithography is conducted. A topcoat composition solution must be applied without attacking the resist film, and also be soluble in the alkali developing solution such as TMAH.

Patent Publication 1 states that a polymer which contains a fluorine-containing monomer represented by formula [1]

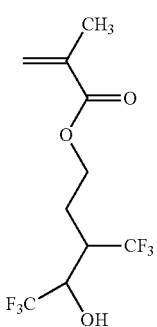

as its component is useful as a raw material of a removable temporary fixing adhesive for its low surface energy.

Furthermore, Patent Publication 2 states that, in a process of producing semiconductors, a polymer produced by using a fluorine-containing monomer represented by the formula [1] as a component, is useful as a topcoat for immersion lithography because its solubility in a developing solution is superior.

Patent Publication 3 states a method for synthesizing a fluorine-containing propanediol represented by formula [2].

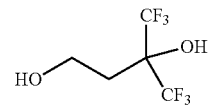

Patent Publication 3 states a method (see the following reaction formula)

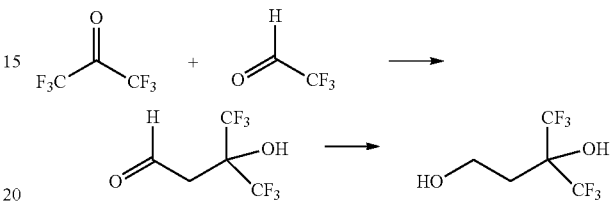

in which 1,1,1,3,3,3-hexafluoroacetone and cesium fluoride are stirred at −78° C., then acetaldehyde is added at room temperature to obtain 4,4,4-trifluoro-3-hydroxy-3-trifluoromethylbutylaldehyde as a fluorine-containing hydroxyaldehyde, and then lithium aluminum hydride is added to conduct a reduction, thereby obtaining 4,4,4-trifluoro-3-hydroxy-3-trifluoromethylbutanol, which belongs to a fluorine-containing propanediol represented by the general formula (2).

Patent Publication 4 discloses a method to gain 4,4,4-trifluoro-3-hydroxy-3-trifluoromethylbutanol (see the following reaction formula)

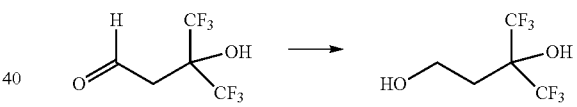

by reducing 4,4,4-trifluoro-3-hydroxy-3-trifluoromethylbutylaldehyde by a contact with hydrogen under a palladium catalyst.

As a method to synthesize 4,4,4-trifluoro-3-hydroxy-3-trifluoromethylbutylaldehyde, Patent Publication 5 states a method in which 1,1,1,3,3,3-hexafluoromethylbutylacetone and n-butyl vinyl ether are reacted to gain 4-butoxy-2,2-bistrifluoromethyloxetane, and then it is hydrolyzed in the presence of acid to gain that (see the following reaction formula).

-continued

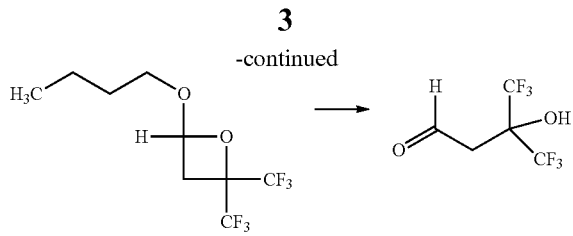

However, the method stated in Patent Publication 3 or 4 has had a problem that it is difficult to pursue it in industrial scale, because of a low selectivity when gaining 4,4,4-trifluoro-3-hydroxy-3-trifluoromethylbutylaldehyde which is a fluorine-containing aldehyde, and therefore yield of 4,4,4-trifluoro-3-hydroxy-3-trifluoromethylbutanol, which is a derivative thereof, is as low as 50%.

Furthermore, there has been a problem that yield of 4,4,4-trifluoro-3-hydroxy-3-trifluoromethylbutylaldehyde, which is an object of the method stated in a Patent Publication 5, is as low as 47%.

Patent Publication 6 discloses a method of producing a diol by a cross aldol reaction of hexafluoroacetone and a carbonyl compound under an acid condition.

PRIOR ART PUBLICATIONS

Patent Publications

Patent publication 1: Japanese Patent Application Publication 2013-84950
Patent Publication 2: International Publication 2011-145663
Patent Publication 3: U.S. Pat. No. 3,440,285
Patent Publication 4: International Publication 2012-112751
Patent Publication 5: Japanese Patent Application Publication 2009-51805
Patent Publication 6: Japanese Patent Application Publication 2005-239710

SUMMARY OF THE INVENTION

The reaction to gain the fluorine-containing hydroxyaldehyde stated in Patent Publication 3 is a low temperature reaction (−78° C.), there is no description of isolating the fluorine-containing hydroxyaldehyde, and yield of the fluorine-containing alcohol (4,4,4-trifluoro-3-hydroxy-trifluoromethylbutanol) produced by reduction is not enough, either. The method to gain the fluorine-containing hydroxyaldehyde (4,4,4-trifluoro-3-hydroxy-3-trifluoromethylbutylaldehyde) stated in Patent Publication 5 does not have an enough yield, either. Both methods are difficult to achieve an industrial practical use.

Thus, it is an object of the present invention to provide a method to produce a fluorine-containing hydroxyaldehyde from a fluorine-containing ketone and an aldehyde compound, which is industrially pursuable.

Furthermore, while including a step of obtaining a fluorine-containing hydroxyaldehyde from a fluorine-containing ketone and an aldehyde compound, which is industrially pursuable, it is an object of the present invention to provide a fluorine-containing propanediol, a fluorine-containing alcohol monomer and its protected body, which are derivatives of the fluorine-containing hydroxyaldehyde, and fluorine-containing polymers prepared by polymerizing these, and resist compositions using the same.

It has been found by the present invention that a fluorine-containing aldehyde compound can be obtained in high yield by reacting hexafluoroacetone with an aldehyde compound in a mild condition (room temperature, about 20° C.) in the presence of an organic base selected from a heterocyclic compound containing a nitrogen(s) in the ring or a tertiary amine.

The present invention contains the following Invention 1 to Invention 15.

[Invention 1]

A method for producing a fluorine-containing hydroxyaldehyde, comprising the step of producing a fluorine-containing hydroxyaldehyde represented by the general formula (1),

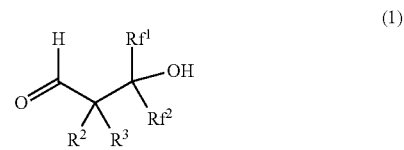

(1)

($Rf^1$ and $Rf^2$ are defined as $Rf^1$ and $Rf^2$ in the general formula (4), and $R^2$ and $R^3$ are defined as $R^2$ and $R^3$ in a general formula (5). $R^2$ and $R^3$ may be connected with each other to form a ring.)
by reacting a fluorine-containing ketone represented by the general formula (4)

(4)

(In the formula, each of $Rf^1$ and $Rf^2$ is independently a $C_{1-6}$ straight-chain, $C_{3-6}$ branched-chain, or $C_{3-6}$ cyclic alkyl group. All or a part of hydrogen atoms in the alkyl group have been replaced with fluorine atom.)
and an aldehyde represented by the general formula (5)

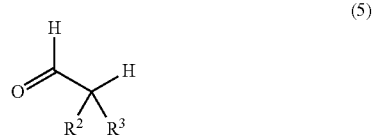

(5)

(In the formula, each of $R^2$ and $R^3$ is independently a hydrogen atom, or a $C_{1-6}$ straight chain, $C_{3-6}$ branched-chain or $C_{3-6}$ cyclic alkyl group. $R^2$ and $R^3$ may be connected to each other to form a ring.)
in the presence of an organic base selected from a heterocyclic compound which contains a nitrogen atom in its ring or a tertiary amine.

[Invention 2]

The method for producing a fluorine containing hydroxyaldehyde of Invention 1, wherein the organic base is at least one organic base selected from the group consisting of pyridine, 2-methylpyridine, 3-methylpyridine, 4-methylpyridine, 2,6-lutidine, 2,4-lutidine, 2,5-lutidine, 3,5-lutidine, 3,4-lutidine, 2,2-bipyridine, 2,4,6-trimethylpyridine, 3,3-bipyridine, 4,4-bipyridine, 2,3-bipyridine, 2,4-bipyridine, 3,4-bipyridine, vinylpyridine, polyvinylpyridine, pyrimidine, pyrazine, pyridazine, triazine, imidazole, pyrazole, quinoline, isoquinoline, acridine, trimethylamine, triethylamine, N,N-diisopropylmethylamine, N,N-diisopropylethylamine, and tributylamine.

[Invention 3]

The method for producing a fluorine-containing hydroxyaldehyde of Invention 1 or Invention 2, wherein both $Rf^1$ and $Rf^2$ are trifluoromethyl groups.

[Invention 4]

The method for producing a fluorine-containing hydroxyaldehyde of Inventions 1-3, wherein both $R^2$ and $R^3$ are hydrogen atoms.

[Invention 5]

A method for producing a fluorine-containing propanediol, comprising:

[1] [a first step] of producing a fluorine-containing hydroxyaldehyde represented by the general formula (1),

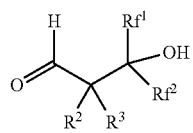

(1)

(In the formula, each of $Rf^1$ and $Rf^2$ is independently a $C_{1-6}$ straight-chain, $C_{3-6}$ branched-chain or $C_{3-6}$ cyclic alkyl group. All or a part of hydrogen atoms in the alkyl group have been replaced with a fluorine atom. Each of $R^2$ and $R^3$ is independently a hydrogen atom, or a $C_{1-6}$ straight chain, $C_{3-6}$ branched-chain or $C_{3-6}$ cyclic alkyl group. $R^2$ and $R^3$ may be connected to each other to form a ring.) by the production method of Invention 1-4; and

[2] [a second step] of producing a fluorine-containing propanediol represented by the general formula (2)

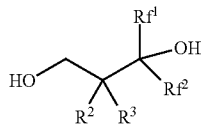

(2)

($Rf^1$, $Rf^2$, $R^2$, and $R^3$ are defined as $Rf^1$, $Rf^2$, $R^2$, and $R^3$ in the general formula (1). $R^2$ and $R^3$ may be connected to each other to form a ring.) by reducing the fluorine-containing hydroxyaldehyde by adding hydrogen in the presence of a metal catalyst, or reducing the fluorine-containing hydroxyaldehyde by a metal hydride.

[Invention 6]

The method for producing a fluorine-containing propanediol of Invention 5, wherein the metal catalyst is a metal catalyst containing at least one metal selected from the group consisting of ruthenium, palladium, rhodium, platinum, nickel, and copper.

[Invention 7]

The method for producing a fluorine-containing propanediol of Invention 5, wherein the metal hydride is at least one metal hydride selected from the group consisting of sodium borohydride, sodium cyanoborohydride, lithium triethylborohydride, lithium borohydride, zinc borohydride, sodium acetoxyborohydride, lithium aluminum hydride, and sodium bis(2-methoxyethoxy)aluminum hydride.

[Invention 8]

A method for producing a fluorine-containing alcohol monomer, comprising: a step of producing a fluorine-containing propanediol represented by the general formula (2),

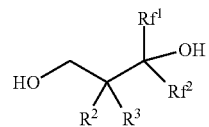

(2)

(In the formula, each of $Rf^1$ and $Rf^2$ is independently a $C_{1-6}$ straight-chain, $C_{3-6}$ branched-chain, or $C_{3-6}$ cyclic alkyl group. All or a part of hydrogen atoms in the alkyl group has been replaced with fluorine atom. Each of $R^2$ and $R^3$ is independently a hydrogen atom, or a $C_{1-6}$ straight-chain, $C_{3-6}$ branched-chain or $C_{3-6}$ cyclic alkyl group. $R^2$ and $R^3$ may be connected to each other to form a ring.) and

[3] a third step of producing a fluorine-containing alcohol monomer represented by the general formula (3)

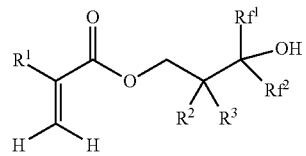

(3)

(In the formula, $R^1$ is defined as $R^1$ in the general formula (6). $Rf^1$, $Rf^2$, $R^2$, and $R^3$ are defined as $Rf^1$, $Rf^2$, $R^2$, and $R^3$ in the general formula (2). $R^2$ and $R^3$ may be connected to each other to form a ring.)

by reacting the fluorine-containing diol with an acrylating agent represented by the general formula (6)

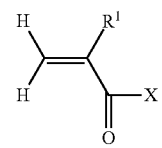

(6)

(In the formula, $R^1$ is a hydrogen atom, a methyl group, a fluorine atom, or a trifluoromethyl group. X is F, Cl or the general formula (7)

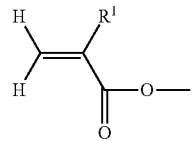

(7)

(In the formula, $R^1$ is defined as $R^1$ in the general formula (6))).

[Invention 9]

A method for producing a fluorine-containing monomer, comprising: a step of producing the fluorine-containing alcohol monomer represented by the general formula (3)

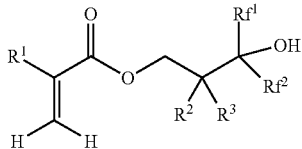

(3)

(In the formula, $R^1$ is defined as $R^1$ in the general formula (6). $Rf^1$, $Rf^2$, $R^2$, and $R^3$ are defined as $Rf^1$, $Rf^2$, $R^2$, and $R^3$ in the general formula (2). $R^2$ and $R^3$ may be connected to each other to form a ring.) by the production method of Invention 8; and

[4] [a forth step] of producing a fluorine-containing monomer represented by the general formula (8)

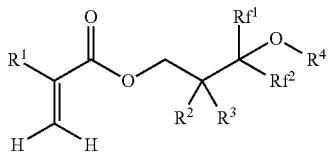

(8)

(In the formula, $R^1$ is defined as $R^1$ in the general formula (6). $Rf^1$, $Rf^2$, $R^2$, and $R^3$ are defined as $Rf^1$, $Rf^2$, $R^2$, and $R^3$ in the general formula (2). $R^2$ and $R^3$ may be connected to each other to form a ring. $R^4$ is a $C_{1-25}$ straight chain, $C_{3-25}$ branched chain, or cyclic alkyl group. It may include a double bond. Carbon atoms in $R^4$ may be replaced by at least one oxygen atom, nitrogen atom, or sulfur atom.) by replacing the hydrogen atom of the hydroxyl group in the fluorine-containing alcohol monomer represented by the general formula (3) with $R^4$ to protect the hydroxyl group.

[Invention 10]

A fluorine-containing polymer comprising a repeating unit represented by the general formula (9)

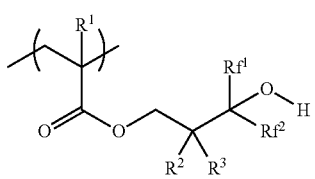

(9)

(In the formula, $R^1$, $Rf^1$, $Rf^2$, $R^2$, and $R^3$ are defined as $R^1$, $Rf^1$, $Rf^2$, $R^2$, and $R^3$, in the general formula (3). $R^2$ and $R^3$ may be connected to each other to form a ring.) prepared by a polymerization of the fluorine-containing alcohol monomer represented by the general formula (3) produced by the method of Invention 8.

[Invention 11]

A fluorine-containing polymer comprising a repeating unit represented by the general formula (10)

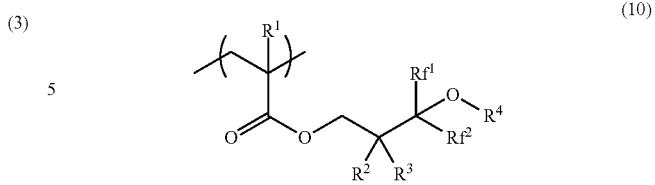

(10)

(In the formula, $R^1$, $Rf^1$, $Rf^2$, $R^2$, $R^3$, and $R^4$ are defined as $R^1$, $Rf^1$, $Rf^2$, $R^2$, $R^3$, and $R^4$ in the general formula (8). $R^2$ and $R^3$ may be connected to each other to form a ring.) prepared by a polymerization of the fluorine-containing monomer represented by the general formula (8) produced by the method of Invention 9.

[Invention 12]

The fluorine-containing polymer of Invention 10 or 11, wherein $Rf^1$ and $Rf^2$ are trifluoromethyl groups, and $R^2$ and $R^3$ are hydrogen atoms.

[Invention 13]

The fluorine-containing polymer of Inventions 10-12, further comprising a repeating unit that has an acid-labile group or an adhesive group.

[Invention 14]

A resist composition comprising the fluorine-containing polymer of Inventions 10-13.

[Invention 15]

The resist composition of Invention 14, comprising at least one of an acid generator, a basic compound, or an organic solvent.

ADVANTAGEOUS EFFECTS OF THE INVENTION

In a method to gain a fluorine-containing hydroxyaldehyde from a fluorine-containing ketone and an aldehyde, a method of producing a fluorine-containing hydroxyaldehyde in the present invention is capable of gaining a high yield of a fluorine-containing hydroxyaldehyde at a mild condition by using an organic base selected from a heterocyclic compound which contains a nitrogen atom(s) in its ring or a tertiary amine as a catalyst.

From the obtained-fluorine-containing hydroxyaldehyde, it is possible to gain a fluorine-containing propanediol which is a derivative of the fluorine-containing hydroxyaldehyde, a fluorine-containing alcohol monomer and its protected body, and fluorine-containing polymers prepared by polymerizing these. The fluorine-containing polymer is useable as a resist composition.

DETAILED DESCRIPTION

Each construction and its combination in the following embodiments are examples, and adding, omitting, substituting and other alternations of the construction can be done in an extent of not deviating from the purport of the present invention. Furthermore, the present invention will not be limited by embodiments, but by only the scope of the claim.

Methods for producing a fluorine-containing hydroxyaldehyde represented by the general formula (1), a fluorine-containing propanediol represented by the general formula (2), and a fluorine-containing alcohol monomer represented by the general formula (3) of the present invention are production methods based on a first step of gaining a fluorine-containing hydroxyaldehyde represented by the general formula (1) as an intermediate compound by reacting a fluorine-containing ketone represented by the general formula (4) and an aldehyde represented by the general formula (5) in the presence of an organic base selected from a heterocyclic compound which contains a nitrogen atom(s) in its ring or a tertiary amine. By adopting the first step, it is possible to obtain a fluorine-containing alcohol monomer represented by the general formula (3) with a high yield, based on a fluorine-containing ketone represented by the general formula (4) and an aldehyde represented by the general formula (5) as the raw material compounds, compared with conventional methods.

1. A Method for Producing a Fluorine-Containing Hydroxyaldehyde Represented by the General Formula (1).

A method for producing a fluorine-containing hydroxyaldehyde represented by the general formula (1)

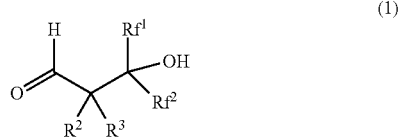

($Rf^1$ and $Rf^2$ are defined as $Rf^1$ and $Rf^2$ in the general formula (4). $R^2$ and $R^3$ are defined as $R^2$ and $R^3$ in the general formula (5). $R^2$ and $R^3$ may be connected to each other to form a ring.) of the present invention is a method for producing a fluorine-containing hydroxyaldehyde, comprising the step of obtaining a fluorine-containing hydroxyaldehyde represented by the general formula (1) as an intermediate compound by reacting as raw material compounds a fluorine-containing ketone represented by the general formula (4)

(In the formula, each of $Rf^1$ and $Rf^2$ is independently a $C_{1-6}$ straight-chain, $C_{3-6}$ branched-chain, or $C_{3-6}$ cyclic alkyl group. All or a part of hydrogen atoms in the alkyl group has been replaced with a fluorine atom(s).) and an aldehyde represented by the general formula (5)

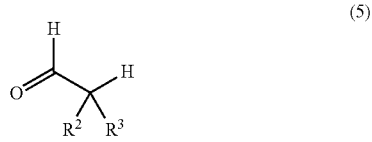

(In the formula, each of $R^2$ and $R^3$ is independently a hydrogen atom, or a $C_{1-6}$ straight chain, $C_{3-6}$ branched-chain or $C_{3-6}$ cyclic alkyl group. $R^2$ and $R^3$ may be connected to each other to form a ring.) in the presence of an organic base selected from a heterocyclic compound which contains a nitrogen atom(s) in its ring or a tertiary amine.

[A Fluorine-Containing Ketone Represented by the General Formula (4)]

In a fluorine-containing ketone represented by the general formula (4) as a raw material compound, hexafluoroacetone in which both $Rf^1$ and $Rf^2$ are trifluoromethyl groups is easy to obtain and a preferable compound to be used in the present invention.

Furthermore, a ketone that does not contain a fluorine atom, such as acetone, is known for its low reactivity. In a fluorine-containing ketone represented by the general formula (4) which is gained by replacing a hydrogen atom(s) of acetone by a fluorine atom, reactivity will get higher if the number of hydrogen atoms replaced by fluorine atoms increases because double bond of carbonyl group will get more easily cleaved as electrons of carbonyl group will get withdrawn by fluorine atoms. Therefore, in a fluorine-containing ketone represented by the general formula (4) gained by replacing hydrogen atoms of acetone by fluorine atoms, hexafluoroacetone is the most reactive.

In an aldehyde represented by the general formula (5), acetaldehyde, in which $R^2$ and $R^3$ are both hydrogens, is easily available and is a preferable compound to be used in the present invention.

[A Method for Producing a Fluorine-Containing Hydroxyaldehyde Represented by the General Formula (1)]

The present step is a reaction to gain a fluorine-containing hydroxyaldehyde represented by the general formula (1) by reacting a fluorine-containing ketone represented by the general formula (4) and an aldehyde represented by the general formula (5) in the presence of an organic base selected from a heterocyclic compound which contains a nitrogen atom(s) in its ring or a tertiary amine. Depending on the substrate, in a condition that a fluorine-containing hydroxyaldehyde represented by the general formula (1) in the reactant does not decompose, high purity of a fluorine-containing hydroxyaldehyde represented by the general formula (1) can be gained by refining it using a method such as column chromatography or distillation.

The present step proceeds well in the presence of an organic base selected from a heterocyclic compound which contains a nitrogen atom(s) in its ring or a tertiary amine. It is a special feature and necessary for the present step to be conducted in the presence of an organic base selected from a heterocyclic compound which contains a nitrogen atom(s) in its ring or a tertiary amine.

In a method for producing the fluorine-containing hydroxyaldehyde, an organic base selected from a heterocyclic compound which contains a nitrogen atom(s) in its ring or a tertiary amine is used as an organic base for additive of the reaction. The heterocyclic compound which contains a nitrogen atom(s) in its ring can be exemplified by pyridine, 2-methylpyridine, 3-methylpyridine, 4-methylpyridine, 2,6-lutidine, 2,4-lutidine, 2,5-lutidine, 3,5-lutidine, 3,4-lutidine, 2,2-bipyridine, 2,4,6-trimethylpyridine, 3,3-bipyridine, 4,4-bipyridine, 2,3-bipyridine, 2,4-bipyridine, 3,4-bipyridine, vinylpyridine, polyvinylpyridine, pyrimidine, pyrazine, pyridazine, triazine, imidazole, pyrazole, quinoline, isoquinoline, or acridine. The tertiary amine can be exemplified by trimethylamine, triethylamine, N,N-diisopropylmethylamine, N,N-diisopropylethylamine, or tributylamine. For its easy availability, easy handling, and having a high catalytic activity, pyridine, 2,6-lutidine, and triethylamine are preferable, and pyridine is particularly preferable. Pyridine is a compound which is hard to use for its odor. In a method for producing a fluorine-containing hydroxyaldehyde of the present invention, when pyridine was purposely used, the effect of accelerating the reaction was notable, and a fluorine-containing hydroxyaldehyde was obtained at high yield. Pyridine is less priced and makes it possible to get a fluorine-containing hydroxyaldehyde at a higher yield than cesium fluoride used in Patent Publication 3. To be more specific, when reacting hexafluoroacetone and acetaldehyde in the presence of pyridine at 70° C., a fluorine-containing hydroxyaldehyde was gained at a high yield of 80%.

Furthermore, in the present step, the hydroxy group in a fluorine-containing hydroxyaldehyde represented by the general formula (1) as the product and the base will form a complex. Relative to 1 equivalent of a fluorine-containing ketone represented by the general formula (4), the amount of the base to be used is 0.05 equivalents or more and 30.0 equivalents or less, preferably 0.3 equivalents or more and 10.0 equivalents or less, and more preferably 1.0 equivalent or more and 3.0 equivalents or less. If it is less than 0.05 equivalents, the reaction will not proceed enough. If it exceeds 30.0 equivalents, the organic base that is not involved in the reaction increases. Therefore, there is no need to add more than 30.0 equivalents.

The present step may be conducted in the presence of a solvent. However, a protic solvent such as alcohol cannot be used. The solvent used in the first reaction is an aprotic solvent, for example, acetonitrile, ethyl acetate, methyl acetate, dimethyl acetamide, N,N-dimethylformamide, dimethyl imidazolidinone, dimethyl sulfoxide, diethyl ether, diisopropyl ether, dibutyl ether, methyl-t-butyl ether, tetrahydrofuran, benzene, toluene, xylene, and mesitylene. These may be used singly. Alternatively, a plurality of solvents may be used together. As they are easily available and handled, preferable solvents are N,N-dimethylformamide, diisopropyl ether, and tetrahydrofuran. It is particularly preferably diisopropyl ether.

The amount of the solvent used in the present step is 0 g or more and 100 g or less, preferably 10 g or less, and more preferably 3 g or less, relative to 1 g of a fluorine-containing ketone represented by the general formula (4). There is no need to add more than 100 g.

In the present step, a fluorine-containing ketone represented by the general formula (4), an aldehyde represented by the general formula (5) and the organic base may be put into the reactor at the same time. Alternatively, the aldehyde may be pressed into a reactor charged with the fluorine-containing ketone and the organic base to prevent the aldehyde from self-condensation. Alternatively, the fluorine-containing ketone and the aldehyde may be pressed at the same time into a reactor charged with the organic base. Alternatively, the base and the aldehyde may be pressed at the same time into a reactor charged with the fluorine-containing ketone.

If the raw material compounds are pressed into a reactor, the time necessary for the pressing is 0 hour or longer and 24 hours or shorter, preferably 2 hours or longer and 20 hours or shorter, and more preferably 3 hours or longer and 18 hours or shorter. The pressing time exceeding 24 hours is neither realistic nor necessary.

The reaction time, which includes the time necessary for the pressing, is 0.5 hours or longer and 24 hours or shorter, preferably 2 hours or longer and 20 hours or shorter, and more preferably 3 hours or longer and 18 hours or shorter. If the time is shorter than 0.5 hours, the reaction is not completed, and a fluorine-containing hydroxyaldehyde represented by the general formula (1) as the product cannot be obtained enough. The reaction time exceeding 24 hours is not realistic. Therefore, exceeding 24 hours is not necessary.

The reaction temperature is 40° C. or higher and 150° C. or lower, preferably 50° C. or higher and 120° C. or lower, more preferably 60° C. or higher and 100° C. or lower. If it is lower than 40° C., the reaction rate is slow, and the polymerization of the aldehyde represented by the general formula (5) proceeds preferentially. Therefore, it is not possible to obtain the fluorine-containing hydroxyaldehyde represented by the general formula (1) in a high yield. By making the reaction temperature 40° C. or higher, the fluorine-containing hydroxyaldehyde can be gained in high yield because the reaction will proceed efficiently. Even if the reaction temperature is over 150° C., it does not make the reaction rate remarkably fast and is not realistic. Therefore, there is no need to make the reaction temperature over 150° C.

After the reaction, to gain a fluorine-containing hydroxyaldehyde represented by the general formula (1) with high purity, it may be washed by an acid diluted with water to remove the organic base.

The acid to be used can be exemplified by hydrochloric acid, sulfuric acid, or phosphoric acid as an inorganic acid, and by formic acid, acetic acid, or methanesulfonic acid as an organic acid.

The amount of the acid used is 0.1 equivalent or more and 2 equivalents or less, preferably 0.5 equivalents or more and 1.6 equivalents or less, and more preferably 0.9 equivalents or more and 1.2 equivalents or less relative to 1 equivalent of the organic base. If the amount of the acid used is less than 0.1 equivalents, the effect of removing the organic base by washing will be low. There is no need to add the acid exceeding 2 equivalents.

The reactor used in the present step is preferably a reactor lined with, for example, tetrafluoroethylene resin, chlorotrifluoroethylene resin, vinylidene fluoride resin, tetrafluoroethylene-perfluoroalkyl vinyl ether copolymer (PFA) resin, or glass, a glass reactor, or stainless steel reactor, which is superior in acid resistance, alkali resistance and solvent resistance.

2. A Method for Producing a Fluorine-Containing Propanediol Represented by the General Formula (2)

As the above step is defined as the first step, it is possible in the fluorine-containing propanediol production method of the present invention to obtain a fluorine-containing propanediol represented by the general formula (2)

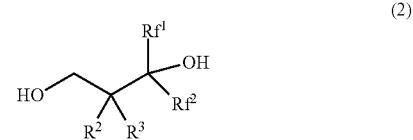
(2)

($Rf^1$ and $Rf^2$ are defined as $Rf^1$ and $Rf^2$ in the general formula (4), $R^2$ and $R^3$ are defined as $R^2$ and $R^3$ in the general formula (5). $R^2$ and $R^3$ may be connected to each other to form a ring.)
by further adding the second step of reducing the fluorine-containing hydroxyaldehyde represented by the general formula (1) by adding hydrogen in the presence of a metal catalyst or by a metal hydride.

[The Second Step]

The second step is a reaction of producing a fluorine-containing propanediol represented by the general formula (2) by reducing a fluorine-containing hydroxyaldehyde represented by the general formula (1) produced in the first step by hydrogen through a metal catalyst, or by reducing a fluorine-containing hydroxyaldehyde represented by the general formula (1) produced in the first step by a metal hydride. The fluorine-containing hydroxyaldehyde may be a reactant that contains the fluorine-containing hydroxyaldehyde.

Furthermore, the reactant of the first step can be used directly for the second step or only after removing the organic base. Prior to the reaction, however, it is optional to conduct a purification by applying a method, such as column chromatography or distillation, under a condition that the fluorine-containing hydroxyaldehyde represented by the general formula (1) in the reactant is not decomposed, thereby using a fluorine-containing hydroxyaldehyde of high purity.

A fluorine-containing propanediol represented by the general formula (2) produced by the second step will be purified by a publicly known method. For example, a crude organic matter can be gained by removing the metal contained in the reaction liquid after the reaction by filtration and then distilling off the solvent in the filtrate. A high purity fluorine-containing propanediol can be gained by subjecting the obtained crude organic matter to a purification such as column chromatography or distillation.

The reactor used in the second step is preferably a reactor lined with, for example, tetrafluoroethylene resin, chlorotrifluoroethylene resin, vinylidene fluoride resin, tetrafluoroethylene-perfluoroalkyl vinyl ether copolymer (PFA) resin, or glass, a glass reactor, or stainless steel reactor, which is superior in acid resistance, alkali resistance and solvent resistance. It is optional to continuously conduct the second step by using the same reactor after the first step without conducting any chemical treatment.

<The First Method of the Second Step (a Reduction by Adding Hydrogen in the Presence of a Metal Catalyst)>

There is explained a method for obtaining a fluorine-containing propanediol represented by the general formula (2) by reducing a fluorine-containing hydroxyaldehyde represented by the general formula (1), which has been produced by the first step, by adding hydrogen in the presence of a metal catalyst (in the following, it may be referred to as the first method).

As the metal catalyst used in the first method, there is suitably used a metal catalyst containing at least one metal selected from the group consisting of ruthenium, palladium, rhodium, platinum, nickel, and copper. In the present invention, the metal catalyst includes the above metal simple substance, a metal catalyst carrying the metal on activated carbon, alumina, silica or clay, etc. as a carrier, and besides a metal salt, metal complex, or metal oxide of the above metal. Furthermore, of these, using plural types of the metal catalyst, it is also possible to conduct the reduction by adding hydrogen to the reaction system. Ruthenium or palladium is preferable, since it is easily available, its handling is easy, and its catalytic activity is high. Ruthenium is particularly preferable.

The amount of the metal catalyst used in the first method in terms of metal atom is normally 0.0001 equivalents or more and 0.05 equivalents or less, preferably 0.0004 equivalents or more and 0.02 equivalents or less, more preferably 0.001 equivalents or more and 0.01 equivalents or less per 1 equivalent of a fluorine-containing hydroxyaldehyde represented by the general formula (1). If the metal catalyst is less than 0.0001 equivalents, there will be no effect as a catalyst and the reactive rate will be slow. Therefore, it will be hard to get a desired amount of a fluorine-containing propanediol represented by the general formula (2). Even if it is added more than 0.05 equivalents, the reaction rate will not be faster. Therefore, such addition is not necessary.

In the first method, the hydrogen pressure when adding hydrogen to the reaction system (into the reaction vessel) is an ordinary pressure (0.1 MPa) or higher and 5 MPa or lower, preferably 0.2 MPa or higher and 4 MPa or lower, more preferably 0.3 MPa or higher and 3 MPa or lower. If the pressure is lower than the ordinary pressure, the reaction rate will be low and it will be hard to gain a desired amount of a fluorine-containing propanediol represented by the general formula (2). Even if the hydrogen pressure is higher than 5 MPa, the reaction rate will not be higher and there might occur a limit in the equipment used for a high pressure.

The first method may be conducted in the presence of a solvent. A usable solvent is preferably benzene, toluene, xylene or mesitylene as an aromatic compound solvent, diethyl ether, methyl-t-butyl ether, diisopropyl ether, or tetrahydrofuran as an ether solvent, methanol, ethanol, propanol, 2-propanol, trifluoroethanol, or 1,1,1,3,3,3-hexafluoro-2-propanol as an alcohol solvent, pyridine or triethylamine as an amine solvent, or water. These may be used singly. Alternatively, a plurality of solvents may be used together. The solvent is preferably toluene, diisopropyl ether, or tetrahydrofuran since it is easily available and easily handled. Diisopropyl ether is particularly preferable.

The amount of the solvent used in the first method is 0 g or more and 100 g or less, preferably 20 g or less, and more preferably 10 g or less per 1 g of a fluorine-containing hydroxyaldehyde represented by the general formula (1). There is no need to add more than 100 g.

The reaction time, in other words reduction time, in the first method is 2 hours or longer and 48 hours or shorter, preferably 4 hours or longer and 30 hours or shorter, more preferably 8 hours or longer and 24 hours or shorter. If the time is shorter than 2 hours, a fluorine-containing hydroxyaldehyde represented by the general formula (1) will not be reduced enough and the yield of a fluorine-containing propanediol represented by the general formula (2) will not high. There is no need to have a reduction time over 48 hours since it is not realistic.

The reaction temperature when conducting the first method is 0° C. or higher and 150° C. or lower, preferably 10° C. or higher and 120° C. or lower, more preferably 30° C. or higher and 100° C. or lower. If the temperature is lower than 0° C., the reaction rate will be low and the yield of a fluorine-containing propanediol represented by general formula (2) will not be high. Furthermore, at a reaction temperature over 150° C., the reaction rate will not get significantly faster. Therefore, there is no need to have a reduction temperature over 150° C. since it is not realistic.

<The Second Method of the Second Step (a Reduction by a Metal Hydride)>

This is a description of the method (hereinafter it may be referred to as the second method) to gain a fluorine-containing propanediol represented by the general formula (2) by reducing a fluorine-containing hydroxyaldehyde represented by the general formula (1) produced by the first step, by a metal hydride.

As the metal hydride used in the second method, there is preferably used at least one metal hydride selected from the group consisting of sodium borohydride, sodium cyanoborohydride, lithium triethylborohydride, lithium borohydride, zinc borohydride, sodium acetoxyborohydride, lithium aluminum hydride, or sodium bis(2-methoxyethoxy)aluminum hydride. Lithium aluminum hydride is particularly preferable.

The reduction can be conducted by using plural types of metal hydrides of these.

The amount of the metal hydride used in the second method in terms of metal atom is 0.1 equivalent or more and 10 equivalent or less, preferably 0.5 equivalent or more and 5 equivalent or less, more preferably 0.8 equivalent or more and 2 equivalent or less per 1 equivalent of a fluorine-containing hydroxyaldehyde represented by the general formula (1). If the metal hydride is less than 0.1 equivalent, it will be hard to get a desired amount of a fluorine-containing propanediol represented by the general formula (2). There is no need to add the metal hydride over 10 equivalent, since the reaction rate will not get faster.

The second method may be conducted in the presence of a solvent. A usable solvent is preferably benzene, toluene, xylene or mesitylene as an aromatic compound solvent, diethyl ether, methyl-t-butyl ether, diisopropyl ether, or tetrahydrofuran as an ether solvent, methanol, ethanol, propanol, 2-propanol, trifluoroethanol, or 1,1,1,3,3,3-hexafluoro-2-propanol as an alcohol solvent, pyridine or triethylamine as an amine solvent, or water. These may be used singly. Alternatively, a plurality of solvents may be used together. An alcohol solvent and water cannot be used as the solvent if the metal hydride is lithium aluminum hydride. The solvent is preferably toluene, diisopropyl ether, or tetrahydrofuran since it is easily available and easily handled. Diisopropyl ether is particularly preferable.

The amount of the solvent used in the second method is 0 g or more and 100 g or less, preferably 20 g or less, more preferably 10 g or less, per 1 g of a fluorine-containing hydroxyaldehyde represented by general formula (1). There is no need to add the solvent over 100 g.

The reaction time needed for the reduction reaction in the second method is 0.1 hours or longer and 10 hours or shorter, preferably 0.5 hours or longer and 8 hours or shorter, more preferably 1 hour or longer and 6 hours or shorter. There is no need to make the reaction time over 10 hours.

The reaction temperature when conducting the second method is −100° C. or higher and 80° C. or lower, preferably −90° C. or higher and 60° C. or lower, more preferably −80° C. or higher and 130° C. or lower. There is no need to make the reaction temperature below −100° C. Furthermore, a reaction temperature over 80° C. is not preferable since there might be a concern that the reaction rate gets too fast, thereby causing by-products.

3. A Method for Producing a Fluorine-Containing Alcohol Monomer Represented by the General Formula (3)

In a method to produce a fluorine-containing alcohol monomer of the present invention, it is possible to obtain a fluorine-containing alcohol monomer represented by the general formula (3)

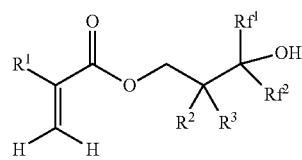

(In the formula, $R^1$ is defined as $R^1$ in the general formula (6). $Rf^1$ and $Rf^2$ are defined as $Rf^1$ and $Rf^2$ in the general formula (4). $R^2$ and $R^3$ are defined as $R^2$ and $R^3$ in the general formula (5). $R^2$ and $R^3$ may be connected to each other to form a ring.)

as a final compound by adding the third step of reacting the fluorine-containing propanediol represented by the general formula (2) with an acrylating agent represented by the general formula (6)

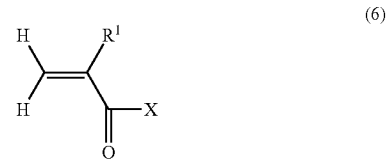

(In the formula, $R^1$ is defined as $R^1$ in the general formula (6). X is F, Cl or the general formula (7)

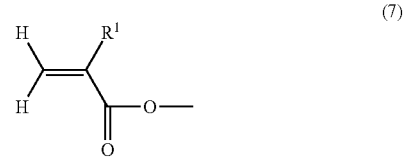

(In the formula, $R^1$ is defined as $R^1$ in the general formula (6).))

The method to produce a fluorine-containing alcohol monomer represented by the general formula (3) comprises the following three steps.

[the first step] A step to gain a fluorine-containing hydroxyaldehyde represented by the general formula (1)

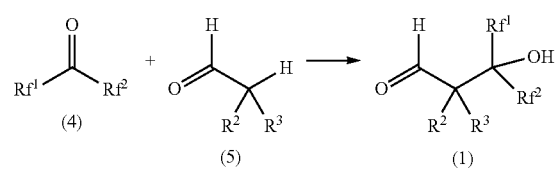

[the second step] A step to gain a fluorine-containing propanediol represented by the general formula (2)

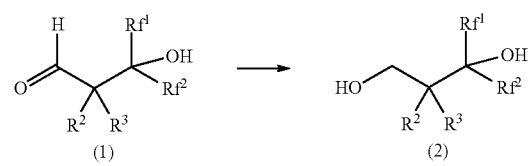

[the third step] A step to gain a fluorine-containing alcohol monomer represented by the general formula (3)

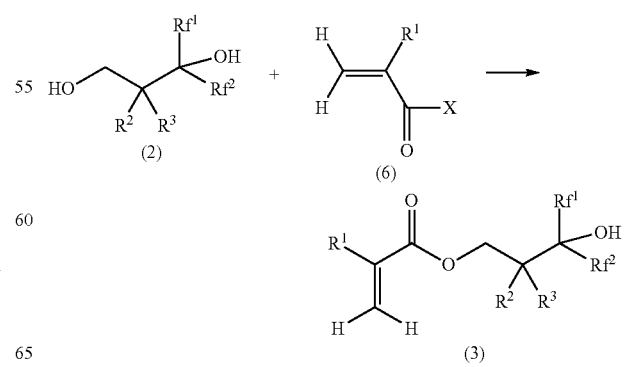

(In the formula, each of Rf¹ and Rf² is independently a $C_{1-6}$ straight-chain, $C_{3-6}$ branched-chain, or fluorine-containing $C_{3-6}$ cyclic alkyl group. $R^1$ is a hydrogen atom, a methyl group, a fluorine atom, or a trifluoromethyl group. Each of $R^2$ and $R^3$ is independently a hydrogen atom, or a $C_{1-6}$ straight-chain, $C_{3-5}$ branched-chain or $C_{3-6}$ cyclic alkyl group. $R^2$ and $R^3$ may be connected to each other to form a ring. X is F, Cl, or a group represented by the general formula (7)

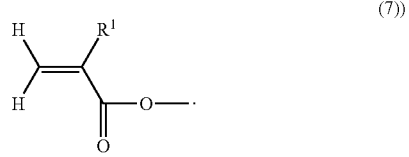

(7)

3.1 the Third Step

The third step is reaction to gain a fluorine-containing alcohol monomer represented by the general formula (3) by reacting a fluorine-containing propanediol represented by the general formula (2) produced by the second step with an acrylating agent represented by the general formula (6). The fluorine-containing diol can be a reactant that contains the fluorine-containing diol.

Furthermore, a reactant in the second step can be used in the third step only by removing metals and metal compounds contained therein by filtration. Prior to the reaction, it is optional to distill out the solvent of the filtrate containing the fluorine-containing propanediol to obtain a crude organic matter and then purify the obtained crude organic matter by column chromatograph or distillation, etc., thereby making a high purity fluorine-containing propanediol to be used in the third reaction.

A fluorine-containing alcohol monomer represented by the general formula (3) produced by the method of the present invention is purified by a publicly known method. For example, a crude organic matter will be gained by treating the reaction liquid with a hydrochloric acid aqueous solution, a sodium carbonate aqueous solution, and water in this order and distilling the solvent out. A highly purified fluorine-containing alcohol monomer can be gained by purifying the crude organic matter by column chromatography, distillation, etc.

The reactor is preferably a reactor lined with, for example, tetrafluoroethylene resin, chlorotrifluoroethylene resin, vinylidene fluoride resin, PFA resin, or glass, a glass reactor, or stainless steel reactor, which is superior in acid resistance, alkali resistance and solvent resistance. It is optional to continuously conduct the third step by using the same reactor after the second step without conducting any chemical treatment.

The third step can be conducted in the presence of base or without using base (in the absence of base). Both cases are described below.

<In the Presence of Base>

Below is a description of the third step in the presence of a base (referred as the first method).

The base used in the first method can be exemplified by pyridine, 2-methylpyridine, 3-methylpyridine, 4-methylpyridine, 2,6-lutidine, 2,4-lutidine, 2,5-lutidine, 3,5-lutidine, 3,4-lutidine, 2,2-bipyridine, 2,4,6-trimethylpyridine, 3,3-bipyridine, 4,4-bipyridine, 2,3-bipyridine, 2,4-bipyridine, 3,4-bipyridine, vinylpyridine, polyvinylpyridine, pyrimidine, pyrazine, pyridazine, triazine, imidazole, pyrazole, quinoline, isoquinoline, acridine, trimethylamine, triethylamine, N,N-diisopropylmethylamine, N,N-diisopropylethylamine, tributylamine, sodium carbonate, potassium carbonate, sodium hydroxide, or potassium hydroxide. It is preferably triethylamine, pyridine, or 2,6-lutidine, since it is easily available and easily handled and has a high catalytic activity. It is particularly preferably triethylamine and pyridine.

The amount of the base used in the first method is 0.3 equivalents or more and 10.0 equivalents or less, preferably 0.6 equivalents or more and 5.0 equivalents or less, more preferably 0.9 equivalents or more and 3.0 equivalents or less, per 1 equivalent of a fluorine-containing propanediol represented by the general formula (2). If it is less than 0.3 equivalents, the reaction will not proceed enough. There is no need to add over 10.0 equivalents because the base not involved in the reaction will increase.

The amount of the acrylating agent represented by the general formula (6) used in the first method is 0.2 equivalents or more and 2.0 equivalents or less, preferably 0.5 equivalents or more and 1.5 equivalents or less, more preferably 0.9 equivalents or more and 1.2 equivalents or less, per 1 equivalent of the fluorine-containing propanediol. If it is less than 0.2 equivalents, the reaction will proceed enough. There is no need to add over 2.0 equivalents because the acrylating agent not involved in the reaction will increase.

The first method may be conducted in the presence of a solvent. Especially, if the acrylating agent is an α-substituted acrylic halide, in which X of an acrylating agent represented by the general formula (6) is a halogen, a hydrohalide of the base as a by-product, such as hydrofluoride or hydrochloride, will be precipitated. Therefore, it is preferable to use a solvent to dissolve the same. Such solvent can be exemplified by benzene, toluene, xylene and methylene as aromatic compounds, n-hexane or n-heptane as an aliphatic solvent, diethyl ether, methyl-t-butyl ether, diisopropyl ether or tetrahydrofuran as an ether solvent, and methylene chloride, chloroform and carbon tetrachloride as halogen solvents. They can be used singly. Alternatively, a plurality of solvents may be used together. It is preferably toluene, diisopropyl ether, or tetrahydrofuran, since they are easily available and easily handled. It is particularly preferably toluene.

The amount of the solvent used in the first method is 0 g or more and 100 g or less, preferably and 50 g or less, more preferably 10 g or less, per 1 g of a fluorine-containing propanediol represented by the general formula (2). There is no need to add the solvent over 100 g.

The reaction time is 0.5 hours or longer and 20 hours or shorter, preferably 1 hour or longer and 10 hours or shorter, more preferably 1.5 hours or longer and 5 hours or shorter. If the time is shorter than 0.5 hours, the reaction will not progress, and it is not possible to obtain a high yield of the fluorine-containing alcohol monomer represented by the general formula (3) as a product. The reaction time longer than 20 hours is not needed since it is not realistic.

The reaction temperature is −50° C. or higher and 200° C. or lower, preferably −30° C. or higher and 150° C. or lower, more preferably 0° C. or higher and 120° C. or lower. If the reaction temperature is below −50° C., the reaction rate will be low, and it is not possible to obtain a high yield of a fluorine-containing alcohol monomer represented by the general formula (3) as a product. There is no need to make the reaction temperature higher than 200° C., since it may cause a fluorine-containing alcohol monomer represented by the general formula (3) as the product and an acrylating agent represented by the general formula (6) to polymerize singly.

Furthermore, the third step may be conducted in the presence of a polymerization inhibitor to prevent the fluorine-containing alcohol monomer as the product and the acrylating agent as a raw material from polymerizing. Such polymerization inhibitor can be exemplified by 2,5-di-t-butylhydroquinone, 1,2,4-trihydroxybenzene, 2,5-bistetramethylbutylhydroquinone, leucoquinizarin, phenothiazine, tetraethylthiuramdisulfide, 1,1-diphenyl-2-picrylhydrazyl, and 1,1-diphenyl-picrylhydrazine. Furthermore, it can be exemplified by N,N'-di-2-naphthyl-p-phenylenediamine (product name, NONFLEX F), N,N'-diphenyl-p-phenylenediamine (product name, NONFLEX H), 4,4'-bis($\alpha,\alpha$-dimethylbenzyl)diphenylamine (product name, NONFLEX DCD), 2,2'-methylene-bis(4-methyl-6 tert-butylphenol) (product name, NONFLEX MBP) and N-(1-methylheptyl)-N'-phenyl-p-phenylenediamine (product name, OZONONE 35), which are commercially available from Seiko Chemical Co., LTD., and ammonium N-nitrosophenylhydroxyamine (product name, Q-1300) and N-nitrosophenylhydroxyamine aluminum salt (product name, Q-1301), which are commercially available from Wako Pure Chemical Industries, LTD.

The amount of the polymerization inhibitor used is 0 equivalent or more and 0.1 equivalents or less, preferably 0.00001 equivalents or more and 0.05 equivalents or less, preferably 0.0001 equivalents or more and 0.01 equivalents or less, per 1 equivalent of the fluorine-containing propanediol as a raw material. Even if the polymerization inhibitor is added over 0.1 equivalent per 1 equivalent of the fluorine-containing propanediol, there is no improvement in the effect of preventing polymerizations of a fluorine-containing alcohol monomer represented by the general formula (3) as the product and an acrylating agent represented by the general formula (6). Therefore, there is no need to add over 0.1 equivalents.

<Under Non-Existence of the Base>

Below is a description of the third step under non-existence of the base (hereinafter it may be referred to as the second method).

The amount of an acrylating agent represented by the general formula (6) used in the second method is 0.2 equivalents or more and 2.0 equivalents or less, preferably 0.5 equivalents or more and 1.5 equivalents or less, more preferably 0.9 equivalents or more and 1.2 equivalents or less, per 1 equivalent of a fluorine-containing propanediol represented by the general formula (2). If it is below 0.2 equivalents, the reaction will not proceed enough. If it exceeds 2.0 equivalents, the acrylating agent not involved in the reaction increases. Therefore, there is no need to add over 2.0 equivalents.

In the second method, it is possible to add an additive to accelerate the reaction. The additive can be exemplified by inorganic acids, such as sulfuric acid and phosphoric acid, sulfonic acids, such as methanesulfonic acid, ethanesulfonic acid, p-toluenesulfonic acid, benzenesulfonic acid and trifluoromethanesulfonic acid, boron trifluoride, or aluminum chloride. It is preferably sulfuric acid, methanesulfonic acid, and trifluoromethanesulfonic acid, since they are easily available and easily handled. It is particularly preferably sulfuric acid and methanesulfonic acid.

The amount of the additive used in the second method is 0.001 equivalents or more and 0.5 equivalents or less, preferably 0.01 equivalents or more and 0.4 equivalent or less, more preferably 0.05 equivalents or more and 0.3 equivalents or less, per 1 equivalent of a fluorine-containing propanediol represented by the general formula (3). If the amount of the additive is less than 0.001 equivalents relative to the fluorine-containing propanediol as the substrate, there is no effect of accelerating the reaction. There is no need to add over 0.5 equivalents.

The second method proceeds without solvent, but solvent may be used. The solvent can be exemplified by benzene, toluene, xylene or methylene as an aromatic compound, n-hexane or n-heptane as an aliphatic solvent, diethyl ether, methyl-t-butyl ether, diisopropyl ether or tetrahydrofuran as an ether solvent, and methylene chloride, chloroform or carbon tetrachloride as a halogen solvent. These may be used singly. Alternatively, a plurality of the solvents may be used together. It is preferably toluene, diisopropyl ether or tetrahydrofuran, since it is easily available and easily handled. It is particularly preferably toluene.

The amount of the solvent used in the second method is 0 g or more and 100 g or less, preferably 60 g or less, more preferably 20 g or less, per 1 g of a fluorine-containing propanediol represented by the general formula (2). There is no need to add over 100 g.

In the second method, a fluorine-containing propanediol represented by the general formula (2), an acrylating agent represented by the general formula (6), and the additive may be added at the same time. Alternatively, it is optional to gradually add the acrylating agent to the fluorine-containing propanediol and the additive, while checking if the reaction temperature increases. Alternatively, it is optional to gradually add the acrylating agent and the additive to the fluorine-containing propanediol.

The time necessary for the addition is 0 hour or longer and 20 hours or shorter, preferably 1 hour or longer and 10 hours or shorter, more preferably 1.5 hours or longer and 5 hours or shorter. There is no need to make the adding time over 20 hours.

The reaction time combined with the time necessary for adding is 0.5 hours or longer and 20.5 hours or shorter, preferably 1 hour or longer and 10.5 hours or shorter, more preferably 1.5 hours or longer and 5.5 hours or shorter. If the time is shorter than 0.5 hours, the reaction will not progress. Therefore, it is not possible to obtain a high yield of the fluorine-containing alcohol monomer represented by the general formula (3) as the product. There is no need to make the reaction time longer than 20.5 hours.

The reaction temperature is 0° C. or higher and 200° C. or lower, more preferably 10° C. or higher and 150° C. or lower, still more preferably 20° C. or higher and 70° C. or lower. If it is below 0° C., the reaction rate will be low, and it is not possible to obtain a high yield of the fluorine-containing alcohol monomer represented by the general formula (3). Furthermore, if exceeding 200° C., it may cause the fluorine-containing alcohol monomer represented by the general formula (3) as the product and the acrylating agent represented by the general formula (6) to polymerize singly. Therefore, there is no need to make it higher than 200° C.

Furthermore, the second method may be conducted in the presence of a polymerization inhibitor to prevent the fluorine-containing alcohol monomer as the product and the acrylating agent as a raw material from polymerizing. The polymerization inhibitor can be exemplified by 2,5-di-t-butylhydroquinone, 1,2,4-trihydroxybenzene, 2,5-bistetramethylbutylhydroquinone, leucoquinizarin, phenothiazine, tetraethylthiuramdisulfide, 1,1-diphenyl-2-picrylhydrazyl, and 1,1-diphenyl-picrylhydrazine. Furthermore, the polymerization inhibitor can be exemplified by N,N'-di-2-naphthyl-p-phenylenediamine (product name, NONFLEX F), N,N'-diphenyl-p-phenylenediamine (product name, NONFLEX H), 4,4'-bis($\alpha,\alpha$-dimethylbenzyl)diphenylamine (product name, NONFLEX DCD), 2,2'-methylene-bis(4- methyl-6 tert-butylphenol) (product name, NONFLEX MBP) and N-(1-methylheptyl)-N'-phenyl-p-phenylenediamine (product name, OZONONE 35), which are commercially available from Seiko Chemical Co., LTD., and ammonium N-nitrosophenylhydroxyamine (product name, Q-1300) and N-nitrosophenylhydroxyamine aluminum salt (product name, Q-1301), which are commercially available from Wako Pure Chemical Industries, LTD.

The amount of the polymerization inhibitor is 0 equivalent or more and 0.1 equivalents or less, preferably 0.00001 equivalents or more and 0.05 equivalents or less, preferably 0.0001 equivalents or more and 0.01 equivalents or less, per 1 equivalent of the fluorine-containing propanediol as a raw material. Even if the polymerization inhibitor is added over 0.1 equivalent per 1 equivalent of the fluorine-containing propanediol, there is no improvement in the effect of preventing polymerizations of a fluorine-containing alcohol monomer represented by the general formula (3) as the product and an acrylating agent represented by the general formula (6). Therefore, there is no need to add over 0.1 equivalents.

4. A Method for Obtaining a Fluorine-Containing Monomer Represented by the General Formula (8)

It is possible to obtain a fluorine-containing monomer represented by the general formula (8) by the forth step of replacing the hydroxyl group of the fluorine-containing alcohol monomer represented by the general formula (3) by $R^4$ to make a protective group.

[About the Forth Step]

To use the polymer in a resist use, it is preferable to adjust affinity to water or the developing solution, or water repellency, or solubility in solvent. For the adjustment, it is preferable by the fourth step to produce a fluorine-containing monomer represented by the general formula (8) by replacing the hydroxyl group of a fluorine-containing alcohol monomer represented by the general formula (3) by $R^4$ to make a protective group. If an acid labile protective group is used as the protective group, it is also possible to raise solubility in the developing solution by the release caused by an action of a photoacid generator during exposure.

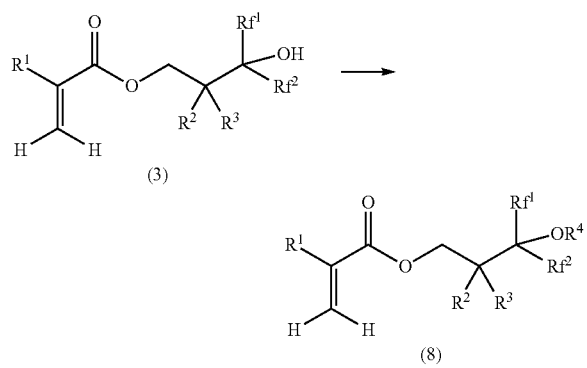

(In the formula, $R^1$ is defined as $R^1$ in the general formula (6). $Rf^1$ and $Rf^2$ are defined as $Rf^1$ and $Rf^2$ in the general formula (4). $R^2$ and $R^3$ are defined as $R^2$ and $R^3$ in the general formula (5). $R^2$ and $R^3$ may be connected to each other to form a ring. $R^4$ is a $C_{1-25}$ straight chain, or $C_{3-25}$ branched chain or cyclic alkyl group and may contain a double bond. A carbon atom(s) contained in $R^4$ may be replaced with at least one atom of oxygen atom, nitrogen atom, or sulfur atom.)

It is possible to obtain a fluorine-containing monomer represented by the general formula (8) by subjecting the hydrogen atom in the hydroxyl group of a fluorine-containing monomer represented by the general formula (3) to a replacement reaction with $R^4$, for example, by using a chloride of $R^4$. To be more specific, it is possible to obtain a fluorine-containing monomer represented by the general formula (8) by subjecting the hydrogen atom in the hydroxyl group of a fluorine-containing monomer represented by the general formula (3) to a replacement reaction by using methoxymethyl chloride, in which $R^4$ is a methoxymethyl group, in the presence of an organic base, for example, pyridine or particularly preferably diisopropylethylamine. It is possible to take a fluorine-containing monomer represented by the general formula (8) from a reactant obtained by the replacement reaction by using column chromatography, etc.

To be specific, the protective group $R^4$ can be exemplified by hydrocarbon groups, alkoxycarbonyl groups, acetal groups, and acyl groups. The hydrocarbon groups are preferably $C_{1-25}$ straight chain, $C_{3-25}$ branched chain or cyclic hydrocarbon groups or aromatic hydrocarbon groups. They can be exemplified by methyl group, ethyl group, propyl group, isopropyl group, cyclopropyl group, n-propyl group, iso-propyl group, sec-butyl group, tert-butyl group, n-pentyl group, cyclopentyl group, sec-pentyl group, neopentyl group, hexyl group, cyclohexyl group, ethylhexyl group, norbornyl group, adamantly group, vinyl group, allyl group, butenyl group, pentenyl, group, ethynyl group, phenyl group, benzyl group, or 4-methoxybenzyl group. The alkoxycarbonyl groups can be exemplified by tert-butoxycarbonyl group, tert-amyloxycarbonyl group, methoxycarbonyl group, ethoxycarbonyl group, or i-propoxycarbonyl group, etc. The acetal groups can be exemplified by methoxymethyl group, ethoxymethyl group, methoxyethoxymethyl group, ethoxyethyl group, butoxyethyl group, cyclohexyloxyethyl group, benzyloxyethyl group, phenethyloxyethyl group, ethoxypropyl group, benzyloxypropyl group, phenethyloxypropyl group, ethoxybutyl group or ethoxyisobutyl group, and groups containing the ether groups, or cyclic ether groups such as tetrahydrofuranyl group or tetrahydropyranyl group. The acyl groups can be exemplified by acetyl group, propionyl group, butyryl group, heptanoyl group, hexanoyl group, valeryl group, pivaloyl group, isovaleryl group, lauryloyl group, myristoyl group, palmitoyl group, stearoyl group, oxalyl group, malonyl group, succinyl group, glutaryl group, adipoyl group, piperoyl group, suberoyl group, azelaoyl group, sebacoyl group, acryloyl group, propioloyl group, methacryloyl group, crotonoyl group, oleoyl group, maleoyl group, fumaroyl group, mesaconoyl group, campholoyl group, benzoyl group, phthaloyl group, isophthaloyl group, terephthaloyl group, naphthoyl group, toluoyl group, hydroatropoyl group, atropoyl group, cinnamoyl group, furoyl group, thenoyl group, nicotinoyl group, or isonicotinoyl group, etc. Hydrogen atoms of these groups may partially or entirely be replaced with a fluorine atom(s).

A fluorine-containing monomer represented by the general formula (8) can be gained by replacing the hydrogen atom of the hydroxyl group of a fluorine-containing monomer represented by the general formula (3) by $R^4$ using a chloride of $R^4$. To be specific, a fluorine-containing monomer represented by the general formula (8) can be gained by replacing the hydrogen atom of the hydroxyl group of a fluorine-containing monomer represented by the general formula (3) by using methoxymethyl chloride, in which $R^4$ is a methoxymethyl group as a chloride of $R^4$, in the presence of a base, such as pyridine. It is possible to take a fluorine-containing monomer represented by the general formula (8) from a reactant obtained by the replacement reaction, by a purification such as column chromatography.

5. A Fluorine-Containing Polymer

A fluorine-containing polymer of the present invention is a polymer containing a repeating unit represented by the following general formula (9) obtained by cleavage of a double bond of a fluorine-containing alcohol monomer represented by the general formula (3) obtained by going through the above-mentioned first step, second step and third step and then its homopolymerization or a copolymerization with other monomers, or a fluorine-containing polymer containing a repeating unit represented by the following general formula (10) obtained by cleavage of a double bond of a fluorine-containing alcohol monomer represented by the general formula (8) obtained by going through the above-mentioned first step, second step, third step and fourth step and then its homopolymerization or a copolymerization with other monomers.

The General Formula (9)

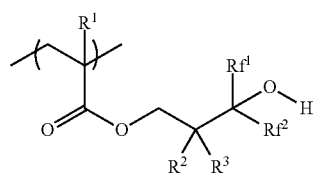

(9)

(In the formula, $R^1$ is defined as $R^1$ in the general formula (6). $Rf^1$, $Rf^2$, $R^2$ and $R^3$ are defined as $Rf^1$, $Rf^2$, $R^2$ and $R^3$ in the general formula (2). $R^2$ and $R^3$ may be connected to each other to form a ring.)

The General Formula (10)

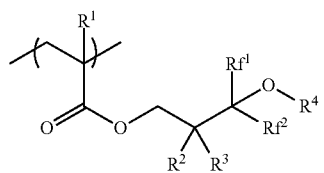

(10)

(In the formula, $R^4$ is defined as $R^4$ in the general formula (6). $Rf^1$, $Rf^2$, $R^2$ and $R^3$ are defined as $Rf^1$, $Rf^2$, $R^2$ and $R^3$ in the general formula (2). $R^2$ and $R^3$ may be connected to each other to form a ring. $R^4$ is defined as in the general formula (8))

It is particularly preferable that the fluorine-containing polymer containing a repeating unit (9) or (10) is a fluorine-containing polymer in which $R^2$ and $R^3$ are hydrogen atoms and RV and $Rf^2$ is trifluoromethyl groups.

5.1 Copolymerizable Monomers

There are shown other monomers that are copolymerizable with a fluorine-containing alcohol monomer represented by the general formula (3) or a polymerizable fluorine-containing monomer represented by the general formula (8).

These monomers can be exemplified by at least one monomer selected from methacrylic acid esters, acrylic acid esters, fluorine-containing acrylic acid esters, fluorine-containing methacrylic acid esters, maleic anhydride, styrene compounds, fluorine-containing styrene compounds, vinyl ethers, fluorine-containing vinyl ethers, allyl ethers, fluorine-containing allyl ethers, olefins, fluorine-containing olefins, norbornene compounds, fluorine-containing norbornene compounds, sulfur dioxide, vinyl silanes, vinyl sulfonic acid, or vinyl sulfonic acid esters.

The acrylic acid esters or the methacrylic acid esters can be exemplified by methyl acrylate, methyl methacrylate, ethyl acrylate, ethyl methacrylate, n-propyl acrylate, n-propyl methacrylate, isopropyl acrylate, isopropyl methacrylate, n-butyl acrylate, n-butyl methacrylate, isobutyl acrylate, isobutyl methacrylate, n-hexyl acrylate, n-hexyl methacrylate, n-octyl acrylate, n-octyl methacrylate, 2-ethylhexyl acrylate, 2-ethylhexyl methacrylate, lauryl acrylate, lauryl methacrylate, 2-hydroxyethyl acrylate, 2-hydroxyethyl methacrylate, 2-hydroxypropyl acrylate and 2-hydroxypropyl methacrylate, an acrylate or methacrylate containing ethylene glycol, propylene glycol or tetramethylene glycol group, acrylamide, methacrylamide, N-methylolacrylamide, N-methylolmethacrylamide, diacetoneacrylamide, acrylonitrile, methacrylonitrile, alkoxysilane, vinylsilane, tert-butyl acrylate, tert-butyl methacrylate, 3-oxocyclohexyl acrylate, 3-oxocyclohexyl methacrylate, adamantyl acrylate, adamantyl methacrylate, methyladamantyl acrylate, methyladamantyl methacrylate, ethyladamantyl acrylate, ethyladamantyl methacrylate, hydroxyadamantyl acrylate, hydroxyadamantyl methacrylate, cyclohexyl acrylate, cyclohexyl methacrylate, tricyclodecanyl acrylate, tricyclodecanyl methacrylate, an acrylate or methacrylate having a ring structure such as lactone ring or norbornene ring, acrylic acid, and methacrylic acid. Also, the acrylic acid ester or methacrylic acid ester having a cyano group at α-position can be cited. Maleic acid, fumaric acid, and maleic anhydride are also copolymerizable.

To be specific, the fluorine-containing acrylic acid or fluorine-containing methacrylic acid is a monomer containing at acrylic α-position a fluorine atom or a group having a fluorine atom(s) or an acrylic acid ester or methacrylic acid ester including a substituent containing a fluorine atom(s) at ester moiety. A fluorine-containing compound containing fluorine at α-position and ester moiety is also preferable. A cyano group may be introduced to α-position. For example, a monomer having a fluorine-containing alkyl group introduced to α-position can be exemplified by a monomer provided with a trifluoromethyl group, trifluoroethyl group or nonafluoro-n-butyl group at α-position of the above-mentioned fluorine-free acrylic acid ester or methacrylic acid ester.

A monomer containing fluorine at ester moiety can be exemplified by an acrylic acid ester or methacrylic acid ester having a unit containing a fluoroalkyl group, such as perfluoroalkyl group or fluoroalkyl group, as an ester moiety, or a unit containing a cyclic structure and fluorine atom in ester moiety, in which the unit has a fluorine-containing benzene ring, fluorine-containing cyclopentane ring, fluorine-containing cyclohexane ring, fluorine-containing cycloheptane ring, etc. prepared by replacing the cyclic structure by, for example, fluorine atom, trifluoromethyl group, hexafluoroisopropyl hydroxyl group, etc. It is also possible to use an acrylic acid or methacrylic acid ester in which ester moiety is a fluorine-containing t-butylester group. It is also possible to use monomers containing these fluorine-containing functional groups and fluorine-containing alkyl groups at α-position. Of such units, as particularly typical ones are specifically shown, they can be exemplified by 2,2,2-trifluoroethylacrylate, 2,2,3,3-tetrafluoropropylacrylate, 1,1,1,3,3,3-hexafluoroisopropylacrylate, heptafluoroisopropylacrylate, 1,1-dihydroheptafluoro-n-butylacrylate, 1,1,5-trihydrooctafluoro-n-pentylacrylate, 1,1,2,2-tetrahydrotridecafluoro-n-octylacrylate, 1,1,2,2-tetrahydroheptadecafluoro-n-decylacrylate, 2,2,2-trifluoroethylmethacrylate, 2,2,3,3-tetrafluoropropylmethacrylate, 1,1,1,3,3,3-hexafluoroisopropylmethacrylate, heptafluoroisopropylmethacrylate, 1,1-dihydroheptafluoro-n-butylmethacrylate, 1,1,5-trihydrooctafluoro-n-pentylmethacrylate, 1,1,2,2-tetrahydrotridecafluoro-n-octylmethacrylate, 1,1,2,2-tetrahydroheptadecafluoro-n-decylmethacrylate, perfluorocyclohexylmethylacrylate, perfluorocyclohexylmethylmethacrylate, 6-[3,3,3-trifluoro-2-hydroxy-2-(trifluoromethyl)propyl]bicyclo[2.2.1]hept-2-yl acrylate, 6-[3,3,3-trifluoro-2-hydroxy-2-(trifluoromethyl)propyl]bicyclo[2.2.1]hept-2-yl 2-(trifluoromethyl)acrylate, 6-[3,3,3-trifluoro-2-hydroxy-2-(trifluoromethyl)propyl]bicyclo[2.2.1]hept-2-yl methacrylate, 1,4-bis(1,1,1,3,3,3-hexafluoro-2-hydroxyisopropyl)cyclohexylacrylate, 1,4-bis(1,1,1,3,3,3-hexafluoro-2-hydroxyisopropyl)cyclohexylmethacrylate, 1,4-bis(1,1,1,3,3,3-hexafluoro-2-hydroxyisopropyl)cyclohexyl, or 2-trifluoromethylacrylate.

As the monomer having a hexafluoroisopropyl hydroxyl group(s) is specifically shown, it can be exemplified by the following compounds.

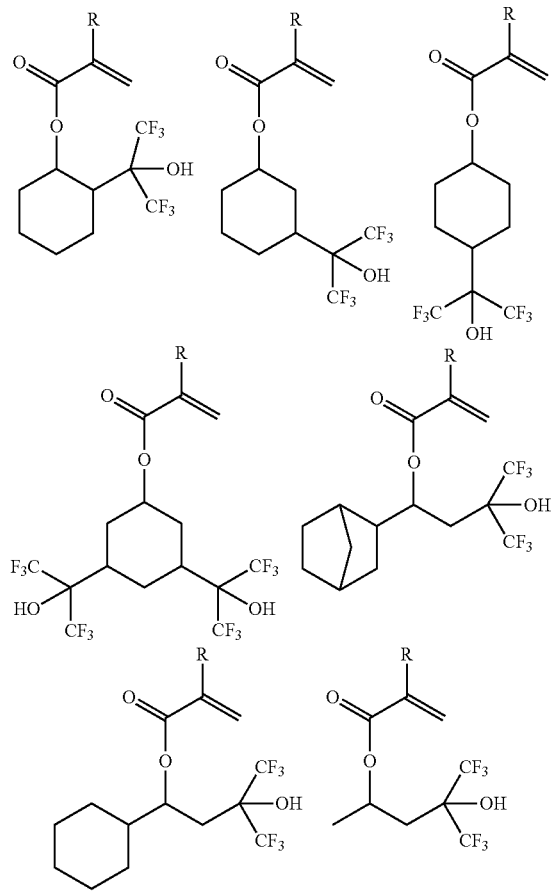

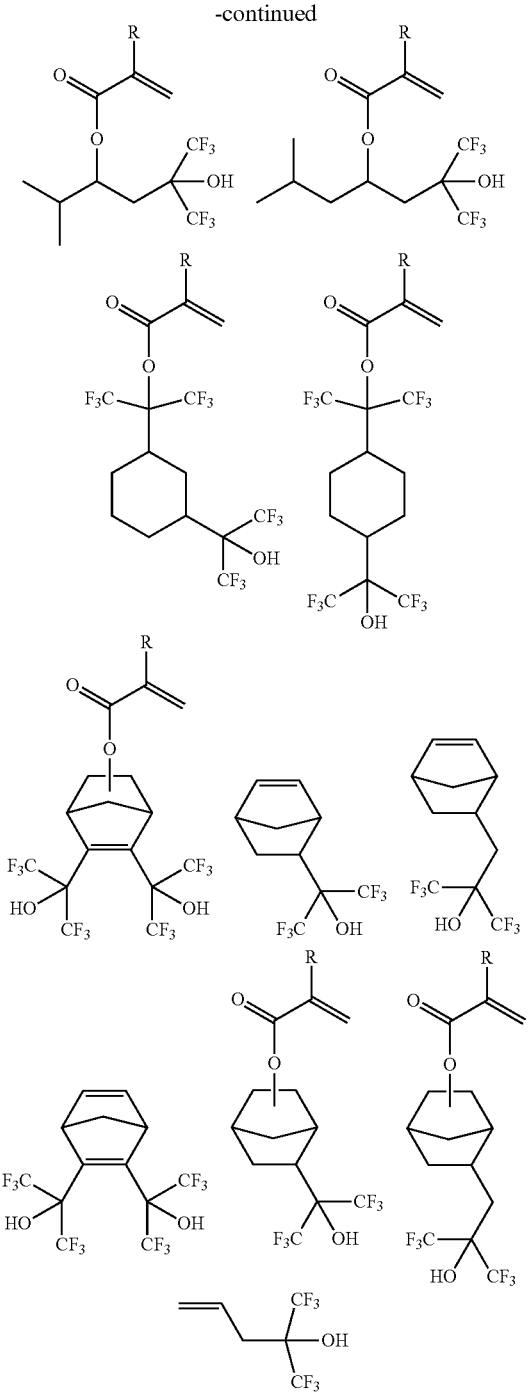

In these formulas, R represents a hydrogen atom, a methyl group, a fluorine atom, or a trifluoromethyl group. Furthermore, the hexafluoroisopropyl hydroxyl group may be protected by a protective group.

As the styrene compound and the fluorine-containing styrene compound, specifically, it is possible to cite as examples styrene, fluorinated styrenes, and hydroxystyrene. More specifically, it is possible to cite as examples pentafluorostyrene, trifluoromethyl styrene, or bistrifluoromethyl styrene. Hydrogen atoms of these compounds may be replaced by a fluorine atom(s) or a functional group(s).

The vinyl ether, the fluorine-containing vinyl ether, the allyl ether, and the fluorine-containing allyl ether can be exemplified by an alkyl vinyl ether or alkyl allyl ether, optionally containing methyl group, ethyl group, propyl group, butyl group, or a hydroxyl group, such as hydroxyethyl group or hydroxybutyl group.

Furthermore, they can be exemplified by cyclic vinyl and allyl ethers having cyclohexyl group, norbornyl group, aromatic ring, or hydrogen or carbonyl bond in its ring structure, and fluorine-containing vinyl ethers and fluorine-containing allyl ethers, in which hydrogens of the functional group have partially or entirely been replaced with a fluorine atom(s).

They can be exemplified by vinyl esters, vinyl silanes, olefins, fluorine-containing olefins, norbornene compounds, fluorine-containing norbornene compounds, and compounds containing other polymerizable unsaturated bonds.

Specifically, the olefins can be exemplified by ethylene, propylene, isobutene, cyclopentene, or cyclohexene. Specifically, the fluorine-containing olefins can be exemplified by vinyl fluoride, vinylidene fluoride, trifluoroethylene, chlorotrifluoroethylene, tetrafluoroethylene, hexafluoropropylene, and hexafluoroisobutene.

The norbornene compounds and the fluorine-containing norbornene compounds can be exemplified by 3-(5-bicyclo[2.2.1]hepten-2-yl)-1,14-trifluoro-2-(trifluoromethyl)-2-propanol, which is a norbornene compound produced by Diels-Alder reaction between a fluorine-containing olefin, allyl alcohol, fluorine-containing allyl alcohol, homoallyl alcohol or fluorine-containing homoallyl alcohol, or an unsaturated compound such as acrylic acid, α-fluoroacrylic acid, α-trifluoromethylacrylic acid, methacrylic acid, acrylic acid ester, methacrylic acid ester, fluorine-containing acrylic acid ester or fluorine-containing methacrylic acid ester, 2-(benzoyloxy)pentafluoropropane, 2-(methoxyethoxymethyloxy)pentafluoropropene, 2-(tetrahydroxypyranyloxy)pentafluoropropene, 2-(benzoyloxy)trifluoroethylene, or 2-(methoxymethyloxy)trifluoroethylene, and cyclopentadiene or cyclohexadiene.

<5.2 A Repeating Unit Having an Acid Labile Group>

The fluorine-containing polymers of Inventions 10-11 may contain a repeating unit having an acid labile group. A repeating unit having an acid labile group can be introduced into the fluorine-containing polymers of Inventions 10-11 by copolymerizing a fluorine-containing alcohol monomer represented by the general formula (3) or a fluorine-containing monomer represented by the general formula (8) with a monomer having an acid labile group.

The purpose for using an acid labile group is to provide positive type photosensitivity and to achieve solubility in an alkali developing solution after exposure to a high energy ray, such as an ultraviolet ray of up to 300 nm in wavelength, excimer laser or X-ray, or electron beam.

A monomer having an acid labile group can be used without a particular limitation, as long as the acid labile group is hydrolyzed and eliminated by an acid generated from the photoacid generator. It suffices that the polymerizable group is alkenyl group or cycloalkenyl group. It is preferably vinyl group, 1-methylvinyl group or 1-trifluoromethylvinyl group. Specifically, monomers having groups represented by the following general formulas (11) to (13) can preferably be used.

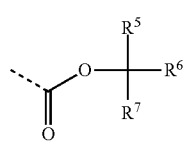
(11)

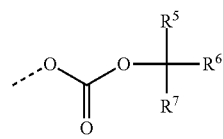
(12)

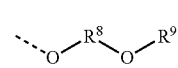
(13)

Herein, each of $R^5$ to $R^9$ is independently a $C_{1-25}$ straight chain, or $C_{3-25}$ branched chain or cyclic alkyl group. It may contain fluorine atom, oxygen atom, nitrogen atom, sulfur atom or hydroxyl group. Two out of $R^5$ to $R^7$ may be connected to each other to form a ring.

Specifically, the groups represented by the general formulas (11) to (13) can be exemplified by groups shown below. Broken lines are bonding arms.

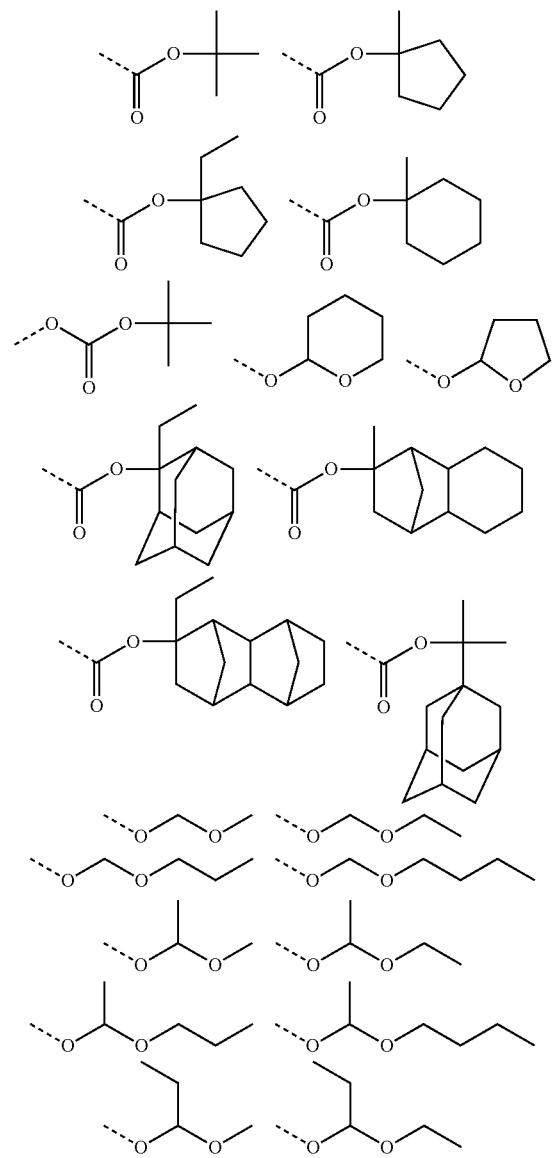

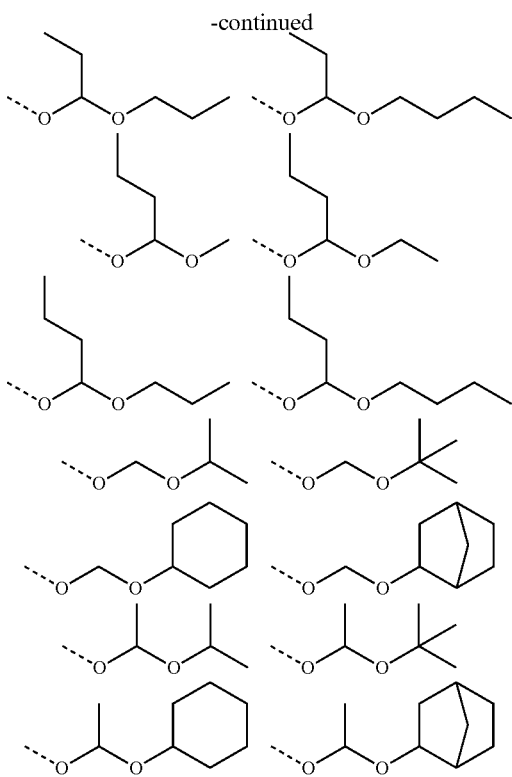

5.3 A Repeating Unit Having an Adhesive Group

The fluorine-containing polymers of Inventions 10-11 may contain a repeating unit having an adhesive group. A repeating unit having an adhesive group can be introduced into the fluorine-containing polymer of Inventions 10-11 by copolymerizing a fluorine-containing alcohol monomer represented by the general formula (3) or a fluorine-containing monomer represented by the general formula (8) with a monomer having an adhesive group.

In the fluorine-containing polymer of Inventions 10-11, it is preferable to introduce an adhesive group containing a lactone structure for the purpose of improving adhesion with the substrate. To introduce an adhesive group, a monomer having a lactone structure is preferably used. Such lactone structure can be exemplified by monocyclic groups, such as a group prepared by removing a hydrogen atom from γ-butyrolactone or mevalonic lactone, and polycyclic groups, such as a group prepared by removing a hydrogen atom from norbornane lactone. By conducting a copolymerization with an acrylic acid ester or methacrylic acid ester having such lactone structure to introduce a lactone structure to the fluorine-containing polymer to make a resist composition, not only it improves adhesion between resist and substrate, but also it increases compatibility with the developing solution. A monomer having an adhesive group may be used singly. Alternatively, a plurality of the monomers may be used together.

5.4 Polymerization Ratio of the Fluorine-Containing Polymer

A fluorine-containing polymer of the present invention may be composed of repeating units derived from several monomers. Its proportion is not particularly limited. For example, the range shown below is preferably used.

The fluorine-containing polymer of the present invention preferably contains 1 mol % or more and 100 mol % or less, more preferably 5 mol % or more and 90 mol % or less, of either a repeating unit (9) produced by polymerization of the fluorine-containing alcohol monomer represented by the general formula (3), or a repeating unit (10) produced by polymerization of the fluorine-containing monomer represented by the general formula (8). Furthermore, the fluorine-containing polymer of the present invention preferably contains 1 mol % or more and 100 mol % or less, more preferably 5 mol % or more and 80 mol % or less, still more preferably 10 mol % or more and 60 mol % or less, of a repeating unit having an acid labile group. Furthermore, it can also contain a repeating unit(s) having no acid-labile group by other polymerizable monomers, preferably by 1 mol % or more and 80 mol % or less, more preferably by 5 mol % or more and 50 mol % or less, of all the repeating units. In case that the repeating unit represented by the general formula (9) or the general formula (10) is contained by less than 1 mol %, it cannot be expected to have an advantageous effect when a resist composition has been made. In case that the repeating unit having an acid labile group is contained by less than 1 mol %, the change of solubility in an alkali developing solution by exposure when a resist composition has been made is too small. With this, it cannot be expected to have a contrast after patterning.

Other polymerizable monomers containing no acid-labile group may be added in order to improve solubility of the fluorine-containing polymer in organic solvents, and etching resistance and mechanical strength of the film. However, the effect cannot be expected, if it is less than 1 mol %.

5.5 A Method for Polymerizing the Fluorine-Containing Polymer

A method for polymerizing the fluorine-containing polymer is not particularly limited, as long as it is a method generally used. Radical polymerization, ionic polymerization, etc. are preferable. It is also possible to use coordinate anionic polymerization, living anion polymerization, cationic polymerization, ring-opening metathesis polymerization, and vinylene polymerization. Each polymerization is specifically explained.

[Radical Polymerization]

Radical polymerization may be conducted by a batch manner, semi-continuous or continuous operation by bulk polymerization, solution polymerization, suspension polymerization or emulsion polymerization in the presence of a radical polymerization initiator or radical initiating source.

The radical polymerization initiator can be used by suitably selecting from azo compounds, peroxide compounds, and redox compounds. To be specific, it can be exemplified by azobisisobutyronitrile, t-butylperoxypivalate, di-t-butylperoxide, i-butyrylperoxide, lauroyl peroxide, succinic acid peroxide, dicinnamylperoxide, di-n-propylperoxydicarbonate, t-butylperoxyallylmonocarbonate, benzoyl peroxide, hydrogen peroxide, or ammonium persulfate.

The reaction vessel used for the polymerization reaction is not particularly limited. Furthermore, it is optional in the polymerization to use a polymerization solvent.

The polymerization solvent is preferably one not blocking the radical polymerization. To be specific, it can be exemplified by ethyl acetate or n-butyl acetate as an ester solvent, acetone or methyl isobutyl ketone as a ketone solvent, toluene or cyclohexane as a hydrocarbon solvent, and methanol, isopropyl alcohol, or ethylene glycol monomethyl ether as an alcohol solvent. It is optional to select water, or an ether, cyclic ether, chlorofluorocarbon or aromatic solvent. These solvents may be used singly. Alternatively, at least two thereof may be used by mixing them together. Furthermore, a molecular weight modifier such as mercaptan may be used together. The reaction temperature of the polymerization reaction is suitably changed according to the radical polymerization initiator or radical polymerization initiating source. It is generally preferably 20° C. or higher and 200° C. or lower, particularly preferably 30° C. or higher and 140° C. or lower.

[Ring-Opening Metathesis Polymerization]

On the other hand, in ring-opening metathesis polymerization, it suffices to use a transition metal catalyst of groups 4-7 in the presence of a cocatalyst and use a publicly-known method in the presence of a solvent.

As a polymerization catalyst, it suffices to suitably select and use a Ti series, V series, Mo series or W series catalyst. To be specific, it can be exemplified by titanium (IV) chloride, vanadium (IV) chloride, vanadium trisacetylacetonato, vanadium bisacetylacetonatodichloride, molybdenum (VI) chloride, and tungsten (VI) chloride. The amount of catalyst is preferably 0.001 mol % or more and 10 mol % or less, more preferably 0.01 mol % or more and 1 mol % or less, relative to the monomers used.

It suffices to suitably select the cocatalyst from alkyl aluminums and alkyl tins. To be specific, it can be exemplified by trimethylaluminum, triethylaluminum, tripropylaluminum, triisopropylaluminum, triisobutylaluminum, tri-2-methylbutylaluminum, tri-3-methylbutylaluminum, tri-2-methylpentylaluminum, tri-3-methylpentylaluminum, tri-4-methylpentylaluminum, tri-2-methylhexylaluminum, tri-3-methylhexylaluminum, or trioctylaluminum, which are trialkylaluminums, dimethylaluminum chloride, diethylaluminum chloride, diisopropylaluminum chloride, or diisobutylaluminum chloride, which are dialkylaluminum halides, methylaluminum dichloride, ethylaluminum dichloride, ethylaluminum diiodide, propylaluminum dichloride, isopropylaluminum dichloride, butylaluminum dichloride, or isobutylaluminum dichloride, which are monoalkylaluminum halides, methylaluminum sesquichloride, ethylaluminum sesquichloride, propylaluminum sesquichloride, or isobutylaluminum sesquichloride, which are alkylaluminum sesquichlorides. It can be exemplified by tetra-n-butyltin, tetraphenyltin, or triphenylchlorotin. The amount of cocatalyst is 100 equivalents or less, preferably 30 equivalents or less, relative to the amount of transition metal catalyst by molar ratio.

Any polymerization solvent will do, as long as it does not block the polymerization reaction. To be specific, it can be exemplified by benzene, toluene or xylene, which is an aromatic hydrocarbon solvent; chlorobenzene or dichlorobenzene, which is a halogenated hydrocarbon solvent; hexane, heptane or cyclohexane, which is a hydrocarbon solvent; and besides carbon tetrachloride, chloroform, methyl chloride, or 1,2-dichloroethane. These solvents may be used singly. Alternatively, at least two thereof may be used by mixing them together. Normally, the reaction temperature is preferably −70° C. or higher and 200° C. or lower, more preferably −30° C. or higher and 60° C. or lower.

[Vinylene Polymerization]

It suffices to conduct a vinylene polymerization in the presence of a cocatalyst by using iron, nickel, rhodium, palladium or platinum as a transition metal catalyst of groups 8-10, or zirconium, titanium, vanadium, chromium, molybdenum or tungsten as a metal catalyst of groups 4-6, in the presence of a solvent.

To be specific, the polymerization catalyst can be exemplified by as a transition metal of groups 8-10 iron(II) chloride, iron(III) chloride, iron(II) bromide, iron(III) bromide, iron(II) acetate, iron(III) acetylacetonato, ferrocene, nickelocene, nickel(II) acetate, nickel bromide, nickel chloride, dichlorohexylnickel acetate, nickel lactate, nickel oxide, nickel tetrafluoroborate, bis(allyl)nickel, bis(cyclopentadienyl)nickel, nickel(II) hexafluoroacetylacetonatotetrahydrate, nickel(II) trifluoroacetylacetonatodihydrate, nickel(II) acetylacetonatotetrahydrate, rhodium(III) chloride, rhodium tris(triphenylphosphine)trichloride, palladium(II) bis(trifluoroacetate), palladium(II) bis(acetylacetonato), palladium(II) 2-ethylhexanoate, palladium(II) bromide, palladium(II) chloride, palladium(II) iodide, palladium(II) oxide, monoacetonitriletris(triphenylphosphine)palladium(II) tretrafluoroborate, tetrakis(acetonitrile)palladium(II) tetrafluoroborate, dichlorobis(acetonitrile)palladium(II), dichlorobis(triphenylphosphine)palladium(II), dichlorobis(benzonitrile)palladium(II), palladium acetylacetonato, palladium bis(acetonitrile)dichloride, palladium bis(dimethylsulfoxide)dichloride or platinum bis(triethylphosphine)hydrobromide, and as a transition metal of groups 4-6 vanadium(IV) chloride, vanadium trisacetylacetonato, vanadium bisacetylacetonatodichloride, trimethoxy(pentamethylcyclopentadienyl)titanium(IV), bis(cyclopentadienyl)titanium dichloride, or bis(cyclopentadienyl)zirconium dichloride. The amount of catalyst is preferably 0.001 mol % or more and 10 mol % or less, more preferably 0.01% or more and 10 mol % or less, relative to the monomers used.

It suffices to suitable select a cocatalyst from alkylaluminoxane and alkylaluminum. To be specific, it can be exemplified by, as a trialkylaluminums, methylaluminoxane (MAO), trimethylaluminum, triethylaluminum, tripropylaluminum, triisopropylaluminum, triisobutylaluminum, tri-2-methylbutylaluminum, tri-3-methylbutylaluminum, tri-2-methylpentylaluminum, tri-3-methylpentylaluminum, tri-4-methylpentylaluminum, tri-2-methylhexylaluminum, tri-3-methylhexylaluminum, or trioctylaluminum; as a dialkylaluminum halide, dimethylaluminum chloride, diethylaluminum chloride, diisopropylaluminum chloride, or diisobutylaluminum chloride; as a monoalkylaluminum halide, methylaluminum dichloride, ethylaluminum dichloride, ethylaluminum diiodide, propylaluminum dichloride, isopropylaluminum dichloride, butylaluminum dichloride, or isobutylaluminum dichloride; as an alkylaluminum sesquichloride, methylaluminum sesquichloride, ethylaluminum sesquichloride, propylaluminum sesquichloride, or isobutylaluminum sesquichloride. The usage of cocatalyst, in the case of methylaluminoxane, is preferably 50 equivalents or more and 500 equivalents or less in terms of aluminum relative to the amount of transition metal catalyst by molar ratio. In the case of other alkylaluminums, it is preferably 1 equivalent or more and 100 equivalents or less, more preferably 30 equivalents or less relative to the amount of transition metal catalyst by molar ratio.

Any polymerization solvent will do, as long as it does not interfere with the polymerization reaction. To be specific, it can be exemplified by, as an aromatic hydrocarbon solvent, benzene, toluene, xylene, chlorobenzene, or dichlorobenzene; as a hydrocarbon solvent, hexane, heptane, nonane, decane, or cyclohexane; as a ketone solvent, acetone, methyl ethyl ketone, methyl isopropyl ketone, methyl isobutyl ketone, cyclohexanone, or cyclopentanone; as an ester solvent, ethyl acetate or butyl acetate; as an alcohol solvent, methanol, ethanol, propanol, isopropanol, butanol, isobutanol, pentanol, hexanol, nonanol, octanol, 1-octanol, 2-octanol, 3-octanol, 4-methyl-2-pentanol, or ethylene glycol; as a halogenated hydrocarbon solvent, carbon tetrachloride, chloroform, methylene chloride, or 1,2-dichloroethane; and besides diethyl ether, diisopropyl ether, tetrahydrofuran, diglyme, propyleneglycolmonomethyletheracetate (PEG-MEA), propyleneglycolmonoethyletheracetate, propyleneglycolmonoethylether, propyleneglycolmonomethylether (PEGME), propyleneglycoldiacetate, ethyl lactate (EL), dimethylformamide, N-methylpyrrolidone, or N-cyclohexylpyrrolidone. These solvents may be used singly. Alternatively, at least two thereof may be used by mixing them together. The reaction temperature is preferably −70° C. or higher and 200° C. or lower, more preferably −40° C. or higher and 80° C. or lower.

5.6 Collection of Fluorine-Containing Polymer

It is possible to obtain the target fluorine-containing polymer by removing an organic solvent or water as a medium from a solution or dispersion containing the fluorine-containing polymer obtained by any of the above polymerization methods, by any method selected from reprecipitation, filtration or heating distillation under reduced pressure.

It is appropriate that the number average molecular weight of the fluorine-containing polymer of the present invention is generally in the range of 1,000-100,000, preferably 3,000-50,000. The molecular weight dispersion is 1-4, preferably 1-2.5.

In the use as a resist, solubility and casting characteristics is changeable depending on the molecular weight. It is possible that a polymer with a high molecular weight has a slow dissolution rate in a developing liquid and that a polymer with a low molecular weight has a fast dissolution rate. It is, however, possible to control the molecular weight by suitably adjusting polymerizing conditions by practical sense of this technical field.

6. A Resist Composition Containing the Fluorine-Containing Polymer

The fluorine-containing polymer of the present invention is preferably used for a photosensitized positive resist composition. As a resist composition, besides (A) the fluorine-containing polymer of the present invention, it is possible to cite (B) a photoacid generator, (C) a basic compound, and (D) a solvent. It may contain (E) a surfactant.

[(B) Photoacid Generator]

It suffices to select a photoacid generator used for a resist composition in the present invention from acid generators for chemically amplified resists. To be specific, it can be exemplified by iodonium sulfonate or sulfonium sulfonate as an onium sulfonate; and besides sulfonic acid esters, N-imidesulfonate, N-oximesulfonate, o-nitrobenzylsulfonate or trismethanesulfonate of pyrogallol.

Acids generated from these photoacid generators by an action of light are alkanesulfonic acids, arylsulfonic acids, and partially or entirely fluorinated arylsulfonic acids or alkanesulfonic acids, and the like. Acid generators that generate partially or entirely fluorinated alkanesulfonic acids are effective because these have a sufficient acid strength against protective groups that are difficult in deprotection. Specifically, it can be exemplified by triphenylsulfonium trifluoromethanesulfonato or triphenylsulfonium perfluoro-n-octanesulfonato.

[(C) Basic Compound]

It is possible to add a basic compound to the resist composition of the present invention. The basic compound has a function of suppressing the diffusion velocity when an acid generated by the acid generator diffuses in a resist film. With this, it can be expected to improve the shape of a resist pattern and obtain the effect of enhancing the stability at the time of post-exposure delay by adjusting the acid diffusion length. It is possible to suitably select the same from aliphatic amines, aromatic amines, heterocyclic amines, or aliphatic polycyclic amines. Secondary or tertiary aliphatic amines are preferable, and alkyl amines are more preferable.

Specifically, it can be exemplified by trimethylamine, triethylamine, tripropylamine, tributylamine, tripentylamine, trihexylamine, triheptylamine, trioctylamine, trinonylamine, tridecanylamine, tridodecylamine, dimethylamine, diethylamine, dipropylamine, dibutylamine, dipentylamine, dihexylamine, diheptylamine, dioctylamine, dinonylamine, didecanylamine, didodecylamine, dicyclohexylamine, methylamine, ethylamine, propylamine, butylamine, pentylamine, hexylamine, heptylamine, octylamine, nonylamine, decanylamine, dodecylamine, diethanolamine, triethanolamine, diisopropanolamine, triisopropanolamine, dioctanolamine, trioctanolamine, aniline, pyridine, picoline, lutidine, bipyridine, pyrrole, piperidine, piperazine, indole, or hexamethylenetetramine. These may be used singly or in combination of two or more kinds. Additionally, the mixing amount thereof is preferably 0.001-2 parts by mass relative to 100 parts by mass of the polymer, more preferably 0.01-1 part by mass relative to 100 parts by mass of the polymer. When the mixing amount is smaller than 0.001 part by mass, the effect of additive is not sufficiently provided. When it exceeds 2 parts by mass, there is a fear that resolution performance and sensitivity become low.

[(D) Solvent]

It suffices that a solvent used for the resist composition in the present invention is capable of making a homogeneous solution by dissolving each component to be added and is suitably selected from resist solvents for the use. Furthermore, at least two kinds of the solvent may be mixed together for the use. The fluorine-containing polymer in the present invention is excellent in solubilities in various solvents. A wide range of solvent selectivity is worthy of special mention.

To be specific, it can be exemplified by acetone, methyl ethyl ketone, cyclopentanone, cyclohexanone, methyl isobutyl ketone, methyl isopentyl ketone, or 2-heptanone as a ketone solvent; isopropanol, butanol, isobutanol, n-pentanol, isopentanol, tert-pentanol, 4-methyl-2-pentanol, 3-methyl-3-pentanol, 2,3-dimethyl-2-pentanol, n-hexanol, n-heptanol, 2-heptanol, n-octanol, n-decanol, s-amyl alcohol, t-amyl alcohol, isoamyl alcohol, 2-ethyl-1-butanol, lauryl alcohol, hexyldecanol, or oleyl alcohol as an alcohol solvent; ethylene glycol, diethylene glycol, propylene glycol, dipropylene glycol, ethyleneglycolmonoacetate, propyleneglycolmonoacetate, dipropyleneglycolmonoacetate, propyleneglycolmonomethylether (PGME), propyleneglycolmonoethylether, propyleneglycolmonopropylether, propyleneglycolmonobutylether, or propyleneglycolmonomethyletheracetate (PGMEA) and its derivative as a polyhydric alcohol solvent; methyl lactate, ethyl lactate (EL), methyl acetate, ethyl acetate, butyl acetate, methyl pyruvate, ethyl pyruvate, methyl methoxypropionate, or ethyl ethoxypropionate as an ester solvent; toluene or xylene as an aromatic solvent; diethyl ether, dioxane, anisole, or diisopropyl ether as an ether solvent; a chlorofluorocarbon, an alternative chlorofluorocarbon, a perfluoro compound, or hexafluoroisopropyl alcohol as a fluorine solvent; and besides a terpene-based petroleum naphtha solvent or a paraffinic solvent as a solvent weak at high boiling point for the purpose of increasing applicability.

It is worthy to specially mention that the fluorine-containing polymer in the present invention is dissolved in n-pentanol, isopentanol, tert-pentanol, 4-methyl-2-pentanol, 3-methyl-3-pentanol, 2,3-dimethyl-2-pentanol, n-hexanol, n-heptanol, 2-heptanol, n-octanol, n-decanol, s-amylalcohol, t-amylalcohol, isoamylalcohol, 2-ethyl-1-butanol, lauryl alcohol, hexyldecanol, or oleyl alcohol, which is a $C_{5-20}$ alcohol solvent, of the above-mentioned alcohol solvents.

Of polyhydric alcohols, due to easy availability and easy handling, it is preferable in these solvents to use propyleneglycolmonomethyletheracetate (PGMEA), propyleneglycolmonomethylether (PGME), or ethyl lactate.

The amount of the solvent added in the resist composition is such that the solid component concentration of the resist composition is preferably 3 mass % or more and 25 mass % or less, more preferably 5 mass % or more and 15 mass % or less. It is possible to adjust the thickness of a resist film to be formed by adjusting the solid component concentration of the resist composition.

[(E) Surfactant]

A surfactant may be added to the resist composition of the present invention. Such surfactant can contain any one or at least two kinds of a fluorine-based surfactant, a silicon-based surfactant, or a surfactant having both of a fluorine atom(s) and a silicon atom(s).

In the following, the present invention is explained in detail by examples, but the present invention is not limited to these embodiments.

Example 1

Production of a Fluorine-Containing Hydroxyaldehyde and a Fluorine-Containing Propanediol A 1-liter autoclave equipped with a thermometer and a stirring blade was charged with 128.6 g (1.63 mol) of pyridine as an additive, followed by sealing. 177.3 g (1.07 mol) of 1,1,1,3,3,3-hexafluoroacetone was added with stirring at room temperature. Heating was conducted until an inside temperature of 70° C., and a mixed solution of 49.4 g (1.12 mol) of acetaldehyde and 266 g of diisopropyl ether was pressed thereinto by spending 5 hours. After standing still for 15 hours, it was exposed to the atmosphere, thereby obtaining 617 g of a reaction liquid.

A reaction formula of the above first step is shown as follows.

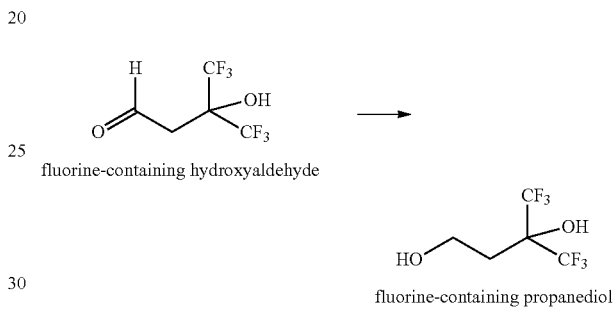

Next, the reaction liquid was washed by using 150 ml of 12 N hydrochloric acid aqueous solution. The separated organic layer was washed three times by using 170 ml of water, thereby obtaining 490 g of an organic layer containing a fluorine-containing acetaldehyde. A fluorine-containing acetaldehyde was collected from the aqueous layer resulting from the hydrochloric acid solution washing and the water washing by repeating three times an extraction operation using 130 g of diisopropyl ether.

In a 1-liter autoclave equipped with a thermometer and a stirring blade was charged with 880 g of a combination of the organic layer resulting from the washing with water and the solution extracted from the aqueous solution resulting from the washing with hydrochloric acid aqueous solution and the washing with water, followed by adding 17 g of a ruthenium carbon (a product containing 50 mass % of water) in which 5 mass % concentration of ruthenium was carried on carbon. After sealing, it was replaced with nitrogen, and then hydrogen was pressed thereinto get a pressure of 1.8 MPa. The autoclave was heated to an inside temperature of 70° C., and stirring was conducted for one whole day. After the stirring, the solution was transferred to a round-bottom flask and subjected to a concentration by distillation using an evaporator, while the bottom portion of the flask was immersed in a water bath, under a condition of a temperature of 30° C. and a vapor pressure of 2 kPa, thereby obtaining 214 g of a concentrate. Furthermore, the concentrate was distilled under a condition of a vapor pressure of 3.0 kPa to 0.5 kPa by using an evaporator and a bath adjusted to a temperature of 60° C. to 70° C., thereby obtaining 181 g of a fluorine-containing propanediol having a purity of 96% by gas chromatography. Yield was 80%.

A reaction formula of the above second step is shown as follows.

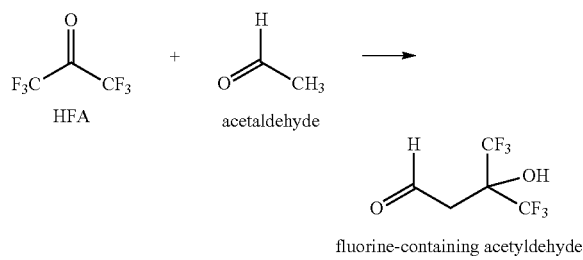

Example 2

Production of a Fluorine-Containing Hydroxyaldehyde and a Fluorine-Containing Propanediol A 300 ml autoclave equipped with a thermometer and a stirring blade was charged with 85.8 g (1.08 mol) of pyridine as an additive and 16.7 g (0.38 mmol) of acetaldehyde, followed by sealing. With stirring, at room temperature, 60.1 g (0.36 mol) of 1,1,1,3,3,3-hexafluoroacetone was added. The autoclave was heated until an inside temperature of 70° C. While maintaining at 70° C., stirring was conducted for 15 hours to conduct the reaction. Then, the autoclave was opened, and 161.4 g of a reaction liquid was obtained.

To 141 g of this, 75 g of diisopropyl ether was added, followed by washing with 166 ml of a 6 N hydrochloric acid aqueous solution and then washing the organic layer three times using 75 ml of water, thereby obtaining 210 g of the organic layer containing a fluorine-containing acetaldehyde. The above reaction is shown by the reaction formula of the above first step.

A 300 ml autoclave equipped with a thermometer and a stirring blade was charged with 210 g of the organic layer, followed by adding 5.2 g of a ruthenium carbon (a product containing 50 mass % of water) in which a ruthenium powder was carried on carbon. After sealing, it was replaced with nitrogen, and then hydrogen was pressed thereinto get a pressure of 1.8 MPa. The autoclave was heated to an inside temperature of 70° C., and stirring was conducted for one whole day. After the stirring, the solution was transferred to a round-bottom flask and subjected to a concentration by distillation using an evaporator, while the bottom portion of the flask was immersed in a water bath, under a condition of a temperature of 30° C. and a vapor pressure of 2 KPa, thereby obtaining 61.4 g of a concentrate. Furthermore, the concentrate was distilled at a bath temperature of 60° C. to 70° C. under a pressure of 3.0 KPa to 0.3 KPa, thereby obtaining 48.0 g of a fluorine-containing propanediol having a purity of 97% by gas chromatography. Yield was 72%. The above reaction is shown by the reaction formula of the above second step.

Example 3

Production of a Fluorine-Containing Hydroxyaldehyde

A 50 ml autoclave having a stirring bar therein was charged with 4.8 g (60.2 mmol) of pyridine as an additive and 1.4 g (31.6 mmol) of acetaldehyde, followed by sealing. Under cooling with dry ice, 5.0 g (30.1 mmol) of 1,1,1,3,3,3-hexafluoroacetone was added. The autoclave was heated to 70° C. While maintaining at 70° C., stirring was conducted for 15 hours, followed by exposure to the atmosphere, thereby obtaining 11.8 g of a reaction liquid. The amount of a fluorine-containing hydroxyaldehyde produced was found to be 4.4 g by an internal standard method using NMR. Yield was 70%.

Example 4

Production of a Fluorine-Containing Alcohol Monomer

A 500 mL, three-neck, glass flask having a stirring bar therein and equipped with a thermometer and a reflux condenser was charged with 181 g (0.85 mol) of the fluorine-containing propanediol produced in Example 1, 127 g (0.82 mol) of methacrylic acid anhydride, 8.2 g (0.09 mol) of methanesulfonic acid, and 1.8 g of 2,2'-methylene-bis(4-methyl-6 tert-butylphenol) (made by Seiko Chemical Co., LTD., product name: NONFLEX MBP). While maintaining at an inside temperature of 60° C., stirring was conducted for 7 hours. 362 g diisopropyl alcohol was added, followed by washing with 492 g of an 8 mass % concentration sodium hydroxide aqueous solution and then washing the organic layer three times by using 181 g of ion exchanged water, thereby obtaining 590 g of the organic layer containing a fluorine-containing alcohol monomer. 590 g of the organic layer was transferred to a round bottom flask and subjected to a concentration by distillation using an evaporator, while it was immersed in a water bath, under a condition to get 40° C. and a vapor pressure of 2 KPa, thereby obtaining 226 g of a fluorine-containing alcohol monomer having a purity of 95% by gas chromatography.

A reaction formula of the above reaction is shown as follows. The above reaction is the third step.

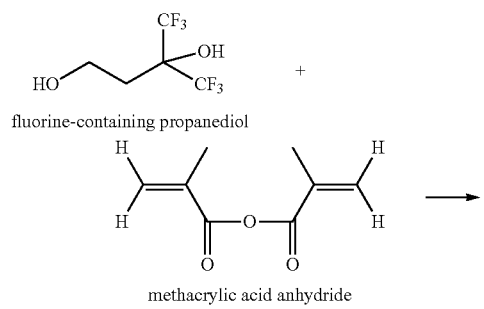

fluorine-containing propanediol methacrylic acid anhydride

-continued

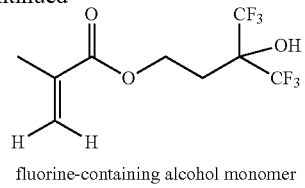

fluorine-containing alcohol monomer

Comparative Example 1

A 1-liter autoclave equipped with a stirring blade was charged with 17.6 g (0.1 mol) of cesium fluoride, followed by filling with nitrogen under atmospheric pressure. After sealing, it was cooled so that the inside temperature of the autoclave became −78° C. While introducing 342 g (2.1 mol) of 1,1,1,3,3,3-hexafluoroacetone, stirring was conducted. After returning to room temperature, 91.5 g (2.1 mol) of acetaldehyde was added. Stirring was conducted for 5 hours, and then 285 g of diethyl ether was added. To prevent heat generation, the reaction liquid taken from the autoclave was gradually added dropwise to a solution prepared by adding 59.7 g (1.57 mol) of lithium aluminum hydride to 1780 g of diethyl ether and then putting into an ice bath. Upon this, in order to decompose an excess of lithium aluminum hydride, 20 g of water was added, and then 300 g of 30 mass % concentration sulfuric acid aqueous solution was added, followed by stirring, then filtration by a filter paper, and then collecting an organic layer. Then, there was repeated five times an operation to collect an organic layer by adding 140 g of diethyl ether to the aqueous layer. The obtained organic layer was dehydrated by magnesium sulfate and then subjected to a concentration by distillation using an evaporator at room temperature under a condition of a vapor pressure of 4 KPa, thereby obtaining a concentrate. The content of the fluorine-containing propanediol in this concentrate was found to be 218 g by an internal standard method using NMR. Yield was 50%.

Comparative Example 2

A 50 ml autoclave having a stirring bar therein was charged with 1.2 g (30.1 mmol) of sodium hydroxide, 1.39 g (31.6 mmol) of acetaldehyde, and 7.5 g of tetrahydrofuran, followed by sealing. While cooling with dry ice, 5.0 g (30.1 mmol) of 1,1,1,3,3,3-hexafluoroacetone was introduced into the autoclave. After returning to room temperature, stirring was conducted for 15 hours. Then, it was opened, thereby obtaining 14.8 g of a reaction liquid. It was confirmed by NMR that the target fluorine-containing hydroxyaldehyde was not identified, resulting in no synthesis.

Comparative Example 3

A 50 ml autoclave having a stirring bar therein was charged with 0.5 g (6.0 mmol) of piperidine ($C_5H_{11}N$) as an alicyclic compound, in which a hydrogen is directly bonded to a nitrogen, 1.39 g (31.6 mmol) of acetaldehyde, and 7.5 g of tetrahydrofuran, followed by sealing. While cooling with dry ice, 5.0 g (30.1 mmol) of 1,1,1,3,3,3-hexafluoroacetone was introduced into the autoclave. After returning to room temperature, stirring was conducted for 15 hours. Then, it was opened, thereby obtaining 13.5 g of a reaction liquid. It was confirmed by NMR that the target fluorine-containing hydroxyaldehyde was not identified, resulting in no synthesis.

Comparative Example 4

A 50 ml autoclave having a stirring bar therein was charged with 8.4 g (90.3 mmol) of aniline ($C_5H_5NH_2$) as an aromatic compound, in which hydrogens are directly bonded to a nitrogen, and 1.32 g (30.1 mmol) of acetaldehyde, followed by sealing. While cooling with dry ice, 5.0 g (30.1 mmol) of 1,1,1,3,3,3-hexafluoroacetone was introduced into the autoclave. The temperature in the autoclave was increased to 70° C. While maintaining at 70° C., stirring was conducted for 15 hours. Then, it was opened, thereby obtaining 14.7 g of a reaction liquid. The target fluorine-containing hydroxyaldehyde was not identified, resulting in no synthesis.

Reference Example 1

A 50 ml autoclave having a stirring bar therein was charged with 4.8 g (60.2 mmol) of pyridine and 1.4 g (31.6 mmol) of acetaldehyde, followed by sealing. While cooling with dry ice, 5.0 g (30.1 mmol) of 1,1,1,3,3,3-hexafluoroacetone was added. At room temperature, stirring was conducted for 15 hours, followed by exposure to the atmosphere, thereby obtaining 11.8 g of a reaction liquid. The amount of the produced fluorine-containing hydroxyaldehyde was found to be 1.3 g by an internal standard method using NMR. The reaction yield was 20%.

Table 1 shows additives, the target compounds, and yields of Examples 1-3, Comparative Examples 1-4, and Reference Example 1.

TABLE 1

| | Additive | Reaction temp. | Result |
|---|---|---|---|
| Example 1 | pyridine | 70° C. | Yield of fluorine-containing propanediol was 80%. |
| Example 2 | | | Yield of fluorine-containing propanediol was 72%. |
| Example 3 | | | Yield of fluorine-containing hydroxyaldehyde was 70%. |
| Com. Ex. 1 | cesium fluoride | Room temp. | Yield of fluorine-containing propanediol was 50%. |
| Com. Ex. 2 | sodium hydroxide | Room temp. | Fluorine-containing hydroxy-aldehyde was not formed. |
| Com. Ex. 3 | piperidine | Room temp. | Fluorine-containing hydroxy-aldehyde was not formed. |
| Com. Ex. 4 | aniline | 70° C. | Fluorine-containing hydroxy-aldehyde was not formed. |
| Ref. Ex. 1 | pyridine | Room temp. | Yield of fluorine-containing hydroxyaldehyde was 20%. |

In Comparative Example 1 as a known method using cesium fluoride as an additive, yield of the target fluorine-containing propanediol was 50%. In contrast with this, in the production methods of Example 1 and Example 2 of the present invention, in which pyridine was used as an additive and the reaction temperature of the cross aldol reaction was 70° C., the fluorine-containing propanediol was obtained in high yields. Furthermore, in Example 3, the fluorine-containing hydroxyaldehyde was obtained in a reaction yield of 70%. In contrast with this, in Comparative Example 2 to Comparative Example 4, the target fluorine-containing hydroxyaldehyde was not formed in the case of using sodium hydroxide, piperidine or aniline. Furthermore, in Reference Example 1, even in the case of using pyridine as an additive, when the reaction was conducted at room temperature, the reaction yield of the fluorine-containing hydroxyaldehyde was as low as 20%.

As shown in Examples 1-3, it is possible by the production method of the present invention to obtain the fluorine-containing hydroxyaldehyde represented by the general formula (3), the fluorine-containing propanediol represented by the general formula (2) or the fluorine-containing alcohol monomer represented by the general formula (3), and the fluorine-containing monomer represented by the general formula (8), in which the hydrogen atom of the hydroxyl group has been replaced with a protective group, in higher yields than those of conventional production methods, from the fluorine-containing ketone represented by the general formula (4) and the aldehyde represented by the general formula (5), by selecting the reaction condition. As shown in Comparative Example 1, in the case of using cesium fluoride, hexafluoroacetone and acetaldehyde were low in conversion, and it was not possible to obtain the fluorine-containing hydroxyacetaldehyde in a high yield. Thus, yield of the fluorine-containing propanediol obtained by reducing the fluorine-containing hydroxyacetaldehyde in the reactant was as low as 50%. However, unexpectedly, as shown in Example 1, a reaction between hexafluoroacetone and acetaldehyde progressed well by using pyridine in place of cesium fluoride, and it was possible to obtain the fluorine-containing hydroxyacetaldehyde in a high yield. Yield of the fluorine-containing propanediol obtained by reducing the reactant was as extremely high as 80%.

[Production of Fluorine-Containing Polymers]

In Examples 5-7, Polymer 1 to Polymer 3 were produced by using the fluorine-containing alcohol monomer obtained by Example 4.

Using HCL-8320GPC made by TOSOH CORPORATION, molecular weight (number average molecular weight Mn) and molecular weight dispersion (the ratio of Mn and weight average molecular weight Mw, Mw/Mn) was measured by connecting an ALPHA-M column and an ALPHA-2500 column made by TOSOH CORPORATION in series and using tetrahydrofuran as an eluent. Refractive index detector was used as a detector. Furthermore, composition of the polymer was determined by $^1$H-NMR and $^{19}$F-NMR measurements.

Example 5

Production of Polymer 1

A glass flask was charged with 14.0 g of the fluorine-containing alcohol monomer obtained by Example 4, 10.9 g of 1-ethyl-1-cyclopentyl methacrylate (MA-ECp), 13.0 g of 5-methacryloyloxy-2,6-norbornanecarbolactone (MNLA), and 0.67 g of n-dodecyl mercaptan as a chain transfer agent. Then, it was charged with 82.8 g of 2-butanone, followed by dissolution to obtain a solution. To the solution, 1.7 g of AIBN (2,2-azobis(isobutyronitrile)) was added as a polymerization initiator, followed by degassing with stirring. After introducing nitrogen gas, the reaction was conducted at 75° C. for 16 hours. The solution after the reaction was added dropwise to 620.0 g of n-heptane, thereby obtaining a white precipitate. This precipitate was separated by filtration and dried under reduced pressure at 60° C., thereby obtaining 36.4 g of a white solid (Polymer 1). As GPC measurement results, Mn was 8,500, and Mw/Mn was 2.1.

The present Polymer 1 contains repeating units derived from the following monomers.

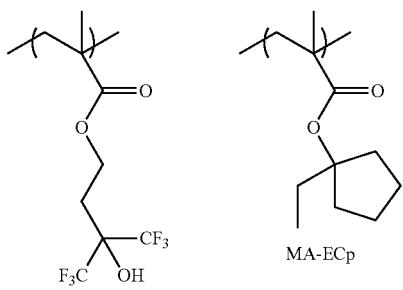

Fluorine-containing alcohol monomer

MA-ECp

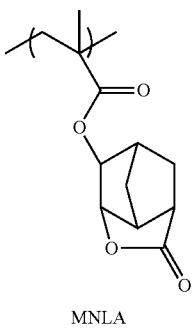

MNLA

Example 6

Production of Polymer 2

A glass flask was charged with 14.0 g of the fluorine-containing alcohol monomer obtained by Example 4, 13.7 g of 2-methyl-2-adamantyl methacrylate (MA-MAD), 9.9 g of γ-butyrolacton-2-yl methacrylate (MA-GBL), and 0.67 g of n-dodecyl mercaptan. Then, it was charged with 82.2 g of 2-butanone, followed by dissolution to obtain a solution. To the solution, 1.6 g of AIBN (2,2-azobis(isobutyronitrile)) was added as a polymerization initiator, followed by degassing with stirring. After introducing nitrogen gas, the reaction was conducted at 75° C. for 16 hours. The solution after the reaction was added dropwise to 620.0 g of n-heptane, thereby obtaining a white precipitate. This precipitate was separated by filtration and dried under reduced pressure at 60° C., thereby obtaining 35.3 g of a white solid (Polymer 2). As GPC measurement results, Mn was 7,800, and Mw/Mn was 2.1.

The present Polymer 2 contains repeating units derived from the following monomers.

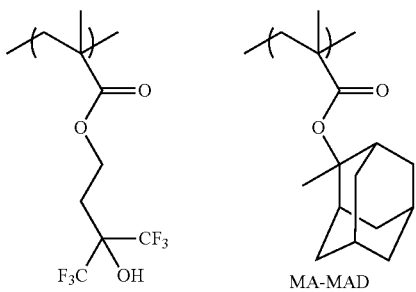

Fluorine-containing alcohol monomer

MA-MAD

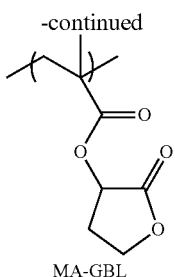

MA-GBL

Example 7

Production of Polymer 3

A glass flask was charged with 22.1 g of the fluorine-containing alcohol monomer obtained by Example 4, 7.2 g of MA-ECp, and 0.45 g of n-dodecyl mercaptan. Then, it was charged with 64.6 g of 2-butanone, followed by dissolution to obtain a solution. To the solution, 1.3 g of AIBN (2,2-azobis(isobutyronitrile)) was added as a polymerization initiator, followed by degassing with stirring. After introducing nitrogen gas, the reaction was conducted at 75° C. for 16 hours. The solution after the reaction was added dropwise to 500.0 g of n-heptane, thereby obtaining a white precipitate. This precipitate was separated by filtration and dried under reduced pressure at 60° C., thereby obtaining 19.8 g of a white solid (Polymer 3). As GPC measurement results, Mn was 11,200, and Mw/Mn was 2.2.

The present Polymer 3 contains repeating units derived from the following monomers.

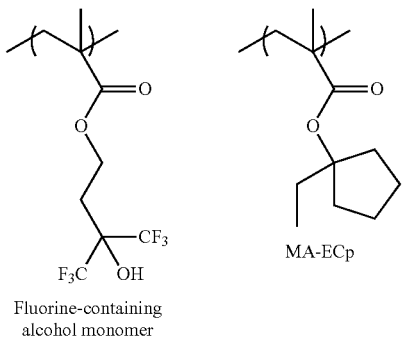

Fluorine-containing alcohol monomer

MA-ECp

Comparative Example 5

Production of Polymer 4

In Example 5, Polymer 4 not falling under the category of the present invention was produced by using MA-HAD in place of the fluorine-containing alcohol monomer obtained by Example 4.

A glass flask was charged with 11.8 g of 3-hydroxy-1-adamantyl methacrylate (MA-HAD), 10.9 g of MA-ECp, 13.0 of MNLA, and 0.67 g of n-dodecyl mercaptan. Then, it was charged with 71.3 g of 2-butanone, followed by dissolution to obtain a solution. To the solution, 1.4 g of AIBN (2,2-azobis(isobutyronitrile)) was added as a polymerization initiator, followed by degassing with stirring. After introducing nitrogen gas, the reaction was conducted at 75° C. for 16 hours. The solution after the reaction was added dropwise to 620.0 g of n-heptane, thereby obtaining a white precipitate. This precipitate was separated by filtration and dried under reduced pressure at 60° C., thereby obtaining 33.0 g of a white solid (Polymer 4). As GPC measurement results, Mn was 8,000, and Mw/Mn was 2.1.

The present Polymer 4 contains repeating units derived from the following monomers.

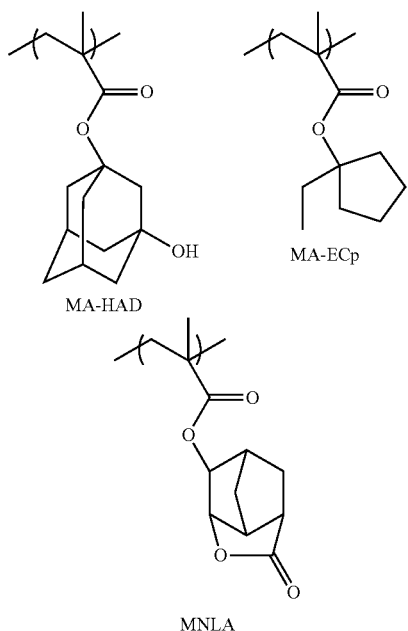

Comparative Example 6

Production of Polymer 5

A glass flask was charged with 10.8 g of 2-ethyl-2-adamantyl (MA-EAD) methacrylate, 10.1 g of MA-GBL, 12.0 of MA-HAD, and 0.54 g of n-dodecyl mercaptan. Then, it was charged with 65.8 g of 2-butanone, followed by dissolution to obtain a solution. To the solution, 1.35 g of AIBN (2,2-azobis(isobutyronitrile)) was added as a polymerization initiator, followed by degassing with stirring. After introducing nitrogen gas, the reaction was conducted at 75° C. for 16 hours. The solution after the reaction was added dropwise to 500.0 g of n-heptane, thereby obtaining a white precipitate. This precipitate was separated by filtration and dried under reduced pressure at 60° C., thereby obtaining 29.6 g of a white solid (Polymer 5) (yield: 90%). As GPC measurement results, Mn was 11,500, and Mw/Mn was 2.1.

The present Polymer 5 is a general resist composition containing repeating units derived from the following monomers.

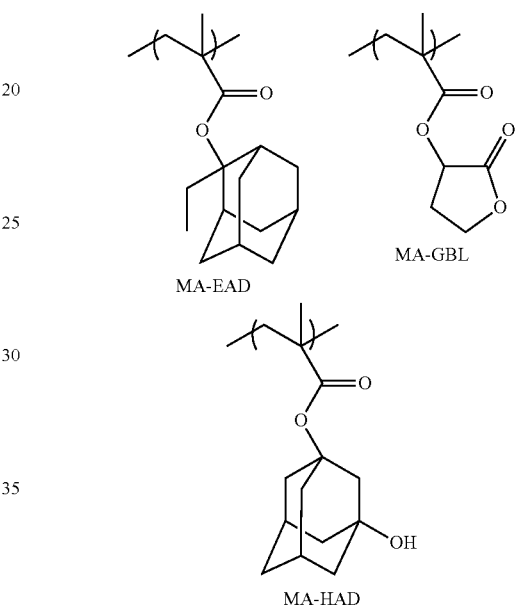

Polymers 1-5 obtained as above by Examples 5-7 and Comparative Examples 5-6 are shown in Table 2. The compositional proportions of the repeating units of the polymers were determined by $^1$H-NMR and $^{19}$F-NMR measurements.

TABLE 2

| | Polymer | Composition proportions (repeating units) (mol %) | | | Molecular weight | | Yield |
|---|---|---|---|---|---|---|---|
| | | | | | Mw | Mw/Mn | (%) |
| Example 5 | Polymer 1 | Fluorine-containing alcohol monomer 32 | MA-ECp 33 | MNLA 35 | 8,500 | 2.1 | 96 |
| Example 6 | Polymer 2 | Fluorine-containing alcohol monomer 29 | MA-MAD 35 | MA-GBL 36 | 7,800 | 2.1 | 94 |
| Example 7 | Polymer 3 | Fluorine-containing alcohol monomer 63 | MA-ECp 37 | — | 11,200 | 2.2 | 68 |
| Com. Ex. 5 | Polymer 4 | MA-HAD 27 | MA-ECp 37 | MNLA 36 | 8,000 | 2.1 | 94 |
| Com. Ex. 6 | Polymer 5 | MA-EAD 35 | MA-GBL 35 | MA-HAD 30 | 11,500 | 2.1 | 90 |

[Evaluation of Resist Compositions]

Examples 8-11 and Comparative Examples 7-8

Evaluation of Polymer 1 obtained in Example 5 and Polymers 4-5 obtained in Comparative Examples 7-8 as resist compositions was conducted.

<Preparation of a Resist Composition and a Manufacture of a Substrate with a Resist Film>

Resist compositions 1-6 were prepared by using Polymer 1 and Polymers 4-5 and by adding a photoacid generator, a basic compound and a solvent to each of them in the proportions shown in Table 3. An anti-reflection film solution (made by NISSAN CHEMICAL INDUSTRIES LTD.; product name: ARC29A) was applied onto a silicon wafer to form a film, followed by baking at 200° C. for 60 seconds to form an anti-reflection film having a film thickness of 78 nm. Each of resists 1-6 was filtered by a 0.2 μm membrane filter and applied onto the anti-reflection film by using a spinner at a rotation speed of 1,500 rpm. Then, it was dried on a hot plate at 100° C. for 90 seconds, thereby preparing a substrate with a resist film formed thereon.

<Contact Angle Measurement>

The contact angle of a waterdrop on the obtained resist film on a silicon wafer was measured by a contact angle meter (Kyowa Interface Science Co. Ltd.). The result is shown in Table 3.

As shown in Table 3, the resist films prepared by using the resist compositions 1-4 containing Polymer 1 shown in Examples 8-11 were higher in contact angle than the resist films using the resist compositions 5-6 containing Polymers 4-5 shown in Comparative Examples 7-8. It is considered that high contact angles were obtained since Polymer 1 contained a hexafluoroisopropanol group. In a lithography using an immersion exposure apparatus, the improvement of a resist film in water repellency makes it possible to prevent water penetration into the resist and suppress the occurrence of watermark defect.

[Resist Film Evaluation]

Examples 12-15 and Comparative Examples 9-10

The resist films prepared by using the above-mentioned Resist Compositions 1-6 were evaluated in terms of developing solution solubility, 4-methyl-2-pentanol solubility, and exposure resolution.

<Evaluation of Developing Solution Solubility>

Silicon wafers with respective resist films formed thereon by using Resist Compositions 1-6 by the above-mentioned procedure were immersed in an alkali developing solution (2.38 weight % tetramethylammonium hydroxide (TMAH) aqueous solution) for 60 seconds at room temperature (about 20° C.) to evaluate solubility in developing solution (developing solution solubility). In an evaluation to see if dissolved in the TMAH aqueous solution, solubility was evaluated by measuring the residue of the resist film after the immersion with an optical interference-type film thickness meter. The results are shown in Table 4. In case that the film disappeared completely, it was judged as "soluble". In case that the film partly remained, it was judged as "partly remained". In case that the film showed almost no change, it was judged as "insoluble".

As shown in Table 4, Resist Compositions 1-6 were each insoluble in the alkali developing solution prior to exposure and became soluble after exposure. From this, all of the resist films prepared by using the resist compositions 1-6 were found to dissolve in the alkali developing solution.

<Evaluation of 4-Methyl-2-Pentanol Solubility>

Silicon wafers with respective resist films formed thereon by using Resist Compositions 1-6 by the above-mentioned procedure were immersed in 4-methyl-2-pentanol (MIBC) for 60 seconds at room temperature (about 20° C.) to evaluate solubility.

The results are shown in Table 4. As shown in Examples 12-15, the resist films obtained from Resist Compositions 1-4 showed solubility in MIBC. Particularly, the resist films obtained from Resist Composition 3 and Resist Composition 4, in which the fluorine content of the fluorine-containing polymer was high, were soluble.

TABLE 3

| | Resist composition | Polymer (parts by mass) | Photoacid generator (parts by mass) | Basic substance (parts by mass) | Solvent (parts by mass) | Contact angle (degree) |
|---|---|---|---|---|---|---|
| Example 8 | Resist composition 1 | Polymer 1 (100) | PAG-1 (5) | Base-1 (1) | PGMEA (900) | 71 |
| Example 9 | Resist composition 2 | Polymer 1 (100) | PAG-1 (5) | Base-1 (1) | PGMEA (900) | 72 |
| Example 10 | Resist composition 3 | Polymer 1 (100) | PAG1 (5) | Base-1 (1) | PGMEA (900) | 76 |
| Example 11 | Resist composition 4 | Polymer 1 (100) | PAG-2 (5) | Base-2 (1) | MIBC (900) | 77 |
| Com. Ex. 7 | Resist composition 5 | Polymer 4 (100) | PAG-1 (5) | Base-1 (1) | PGMEA (900) | 65 |
| Com. Ex. 8 | Resist composition 6 | Polymer 5 (100) | PAG1 (5) | Base-1 (1) | PGMEA (900) | 65 |

PAG-1: triphenylsulfonium nonafluorobutanesulfonate
PAG-2: triphenylsulfonium trifluoromethanesulfonate
Base-1: isopropanolamine
Base-1: triethanolamine
PGMEA: propyleneglycolmonomethyletheracetate
MIBC: 4-methyl-2-pentanol As shown in Comparative Examples 9-10, the resist films obtained from Resist Compositions 5-6 were insoluble in MIBC. Resist Composition 6 (MA-EAD/MA-GBL/MA-HAD series) is a general resist composition.

In a double patterning method where a pattern is formed on the first resist film, then the second resist film is formed, and then an exposure treatment is conducted, it was suggested that, for example, the above-mentioned general-purpose Resist Composition 6 is usable for the first resist film and that resist solutions prepared by dissolving Resist Compositions 1-4 containing Polymer 1 in MIBC are usable as resist solutions for forming the second resist film.

That is, MIBC as a solvent used for the second resist solution does not attack the resist pattern formed on the first resist film. Therefore, it becomes possible to form the second resist film without affecting the first resist pattern.

<Evaluation of Exposure Resolution>

Silicon wafers with respective resist films formed thereon by using Resist Compositions 1-6 by the above-mentioned procedure were heated at 100° C. for 60 seconds to conduct a prebaking of the resist film, followed by exposure to an ultraviolet light having a wavelength of 193 nm through a photomask. After the exposure, while rotating the wafer, pure water was added dropwise for 2 minutes. Then, it was heated at 120° C. for 60 seconds to conduct a post-exposure baking, followed by development with an alkali developing solution.

The obtained resist pattern was observed with a scanning electron microscope (SEM) to evaluate resolution. The results are shown in Table 4.

The resist patterns of Examples 12-15 obtained by using Resist Compositions 1-4 were rectangular patterns, showing a good exposure resolution. In contrast with this, in Comparative Example 9 using Resist Composition 5, it was a pattern with a disordered shape caused by swelling of the resist pattern.

Furthermore, in Reference Example 3 using Resist Composition 6 as a general-purpose resist of a nonfluorinated resin, the resist pattern was inferior in pattern formation due to a strong T-top shape.

TABLE 4

| No. | Resist | Alkali developing solution solubility Unexposed | Alkali developing solution solubility Exposed | Solvent solubility (MIBC) | Exposure resolution |
|---|---|---|---|---|---|
| Example 12 | Resist comp. 1 | insoluble | soluble | Partly remained | Rectangular pattern |
| Example 13 | Resist comp. 2 | insoluble | Soluble | Partly remained | Rectangular pattern |
| Example 14 | Resist comp. 3 | insoluble | Soluble | Soluble | Rectangular pattern |
| Example 15 | Resist comp. 4 | insoluble | Soluble | Soluble | Rectangular pattern |
| Com. Ex. 9 | Resist comp. 5 | insoluble | soluble | Insoluble | Disordered shape pattern |
| Com. Ex. 10 | Resist comp. 6 | insoluble | soluble | Insoluble | Inferior in pattern formation |

MIBC: 4-methyl-2-pentanol

The invention claimed is:

1. A method for producing a fluorine-containing hydroxyaldehyde, comprising the step of producing a fluorine-containing hydroxyaldehyde of general formula (1),

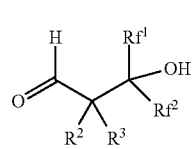

(1)

by reacting a fluorine-containing ketone of general formula (4)

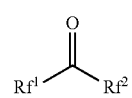

(4)

and an aldehyde of general formula (5)

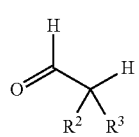

(5)

in the presence of an organic base selected from a heterocyclic compound which contains a nitrogen atom in its ring or a tertiary amine wherein each of $Rf^1$ and $Rf^2$ is independently a $C_{1-6}$ straight-chain, $C_{3-6}$ branched-chain, or $C_{3-6}$ cyclic alkyl group, and all or a part of hydrogen atoms in the alkyl group have been replaced with a fluorine atom;

wherein each of $R^2$ and $R^3$ is independently a hydrogen atom, or a $C_{1-6}$ straight chain, $C_{3-6}$ branched-chain or $C_{3-6}$ cyclic alkyl group, and $R^2$ and $R^3$ may be connected to each other to form a ring.

2. The method for producing a fluorine containing hydroxyaldehyde of claim 1, wherein the organic base is at least one organic base selected from the group consisting of pyridine, 2-methylpyridine, 3-methylpyridine, 4-methylpyridine, 2,6-lutidine, 2,4-lutidine, 2,5-lutidine, 3,5-lutidine, 3,4-lutidine, 2,2-bipyridine, 2,4,6-trimethylpyridine, 3,3-bipyridine, 4,4-bipyridine, 2,3-bipyridine, 2,4-bipyridine, 3,4-bipyridine, vinylpyridine, polyvinylpyridine, pyrimidine, pyrazine, pyridazine, triazine, imidazole, pyrazole, quinoline, isoquinoline, acridine, trimethylamine, triethylamine, N,N-diisopropylmethylamine, N,N-diisopropylethylamine, and tributylamine.

3. The method for producing a fluorine-containing hydroxyaldehyde of claim 1, wherein both $Rf^1$ and $Rf^2$ are trifluoromethyl groups.

4. The method for producing a fluorine-containing hydroxyaldehyde of claim 1, wherein both $R^2$ and $R^3$ are hydrogen atoms.

5. A method for producing a fluorine-containing propanediol, comprising the steps of:

[1] producing a fluorine-containing hydroxyaldehyde of general formula (1), (1)

by the production method of claim 1; and

[2] producing a fluorine-containing propanediol of general formula (2)

(2)

by reducing the fluorine-containing hydroxyaldehyde by adding hydrogen in the presence of a metal catalyst, or reducing the fluorine-containing hydroxyaldehyde by a metal hydride wherein each of $Rf^1$ and $Rf^2$ is independently a $C_{1-6}$ straight-chain, $C_{3-6}$ branched-chain or $C_{3-6}$ cyclic alkyl group, and all or a part of hydrogen atoms in the alkyl group have been replaced with a fluorine atom; each of $R^2$ and $R^3$ is independently a hydrogen atom, or a $C_{1-6}$ straight chain, $C_{3-6}$ branched-chain or $C_{3-6}$ cyclic alkyl group, and $R^2$ and $R^3$ may be connected to each other to form a ring.

6. The method for producing a fluorine-containing propanediol of claim 5, wherein the metal catalyst is a metal catalyst containing at least one metal selected from the group consisting of ruthenium, palladium, rhodium, platinum, nickel, and copper.

7. The method for producing a fluorine-containing propanediol of claim 5, wherein the metal hydride is at least one metal hydride selected from the group consisting of sodium borohydride, sodium cyanoborohydride, lithium triethylborohydride, lithium borohydride, zinc borohydride, sodium acetoxyborohydride, lithium aluminum hydride, and sodium bis(2-methoxyethoxy)aluminum hydride.

8. A method for producing a fluorine-containing alcohol monomer, comprising the steps of:

[1] producing a fluorine-containing propanediol of general formula (2), (2)

by the production method of claim 5; and

[2] producing a fluorine-containing alcohol monomer of general formula (3)

(3)

by reacting the fluorine-containing diol with an acrylating agent of general formula (6)

(6)

wherein each of $Rf^1$ and $Rf^2$ is independently a $C_{1-6}$ straight-chain, $C_{3-6}$ branched-chain, or $C_{3-6}$ cyclic alkyl group, and all or a part of hydrogen atoms in the alkyl group has been replaced with a fluorine atom;

wherein each of $R^2$ and $R^3$ is independently a hydrogen atom, or a $C_{1-6}$ straight-chain, a $C_{3-6}$ branched-chain or $C_{3-6}$ cyclic alkyl group, and $R^2$ and $R^3$ may be connected to each other to form a ring;

wherein $R^1$ is a hydrogen atom, a methyl group, a fluorine atom, or a trifluoromethyl group;

wherein X is F, Cl or the general formula (7), (7)

9. A method for producing a fluorine-containing monomer, comprising:

[1] producing the fluorine-containing alcohol monomer of general formula (3)

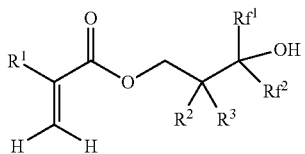
(3)

by the production method of claim 8; and

[2] producing a fluorine-containing monomer of general formula (8)

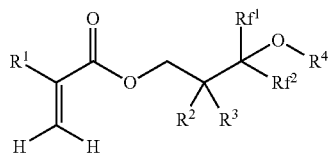
(8)

by replacing a hydrogen atom of a hydroxyl group in the fluorine-containing alcohol monomer of general formula (3) with $R^4$ to protect the hydroxyl group wherein $R^1$ is defined as $R^1$ in the general formula (6); $Rf^1$, $Rf^2$, $R^2$, and $R^3$ are defined as $Rf^1$, $Rf^2$, $R^2$, and $R^3$ in the general formula (2), and $R^2$ and $R^3$ may be connected to each other to form a ring;

$R^4$ is a $C_{1-25}$ straight chain, $C_{3-25}$ branched chain or cyclic alkyl group and may include a double bond, and a carbon atom in $R^4$ may be replaced by an oxygen atom, nitrogen atom, or sulfur atom.

10. A fluorine-containing polymer comprising a repeating unit of general formula (9)

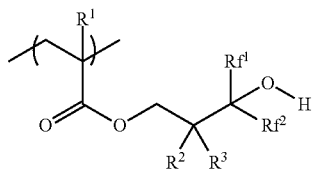
(9)

prepared by a polymerization of the fluorine-containing alcohol monomer of general formula (3) produced by the method of claim 8, wherein $R^1$, $Rf^1$, $Rf^2$, $R^2$, and $R^3$ are defined as $R^1$, $Rf^1$, $Rf^2$, $R^2$, and $R^3$, in the general formula (3), and $R^2$ and $R^3$ may be connected to each other to form a ring, and wherein the fluorine-containing polymer has a number average molecular weight of 1,000 to 100,000.

11. A fluorine-containing polymer comprising a repeating unit of general formula (10)

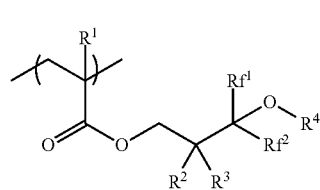
(10)

prepared by a polymerization of the fluorine-containing monomer of general formula (8) produced by the method of claim 9, wherein $R^1$, $Rf^1$, $Rf^2$, $R^2$, $R^3$, and $R^4$ are defined as $R^1$, $Rf^1$, $Rf^2$, $R^2$, $R^3$, and $R^4$ in the general formula (8), and $R^2$ and $R^3$ may be connected to each other to form a ring, and wherein the fluorine-containing polymer has a number average molecular weight of 1,000 to 100,000.

12. The fluorine-containing polymer of claim 10, wherein $Rf^1$ and $Rf^2$ are trifluoromethyl groups, and $R^2$ and $R^3$ are hydrogen atoms.

13. The fluorine-containing polymer of claim 10, further comprising a repeating unit that has an acid-labile group or an adhesive group.

14. A resist composition comprising the fluorine-containing polymer of claim 10.

15. The resist composition of claim 14, comprising at least one of an acid generator, a basic compound, or an organic solvent.

* * * * *